(12) United States Patent
Adachi et al.

(10) Patent No.: US 11,147,460 B2
(45) Date of Patent: Oct. 19, 2021

(54) BODY CONDITION PREDICTING DEVICE, METHOD, AND PROGRAM

(71) Applicant: SHARP KABUSHIKI KAISHA, Sakai (JP)

(72) Inventors: Yoshihisa Adachi, Sakai (JP); Yasuhiro Harada, Sakai (JP); Toshimasa Kuchii, Sakai (JP); Hitoshi Nakamura, Sakai (JP); Kazuyuki Matsuoka, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 196 days.

(21) Appl. No.: 16/301,513

(22) PCT Filed: Apr. 18, 2017

(86) PCT No.: PCT/JP2017/015534
§ 371 (c)(1),
(2) Date: Nov. 14, 2018

(87) PCT Pub. No.: WO2017/199663
PCT Pub. Date: Nov. 23, 2017

(65) Prior Publication Data
US 2019/0282177 A1    Sep. 19, 2019

(30) Foreign Application Priority Data
May 16, 2016   (JP) .............................. JP2016-098202

(51) Int. Cl.
*A61B 5/00*     (2006.01)
*A61B 5/0205*   (2006.01)
(Continued)

(52) U.S. Cl.
CPC ............ *A61B 5/02055* (2013.01); *A61B 5/00* (2013.01); *A61B 5/7275* (2013.01); *A61B 5/742* (2013.01);
(Continued)

(58) Field of Classification Search
CPC ..... A61B 5/7275; A61B 5/00; A61B 5/02055; A61B 5/742; A61B 5/024; A61B 5/443;
(Continued)

(56) References Cited

U.S. PATENT DOCUMENTS

2005/0228242 A1   10/2005  Kawamura et al.
2016/0235374 A1*  8/2016   Miller ................ A61B 5/02055

FOREIGN PATENT DOCUMENTS

JP    2005-319283 A    11/2005
JP    2013-238970 A    11/2013

* cited by examiner

*Primary Examiner* — Erin M Piateski
(74) *Attorney, Agent, or Firm* — ScienBiziP, P.C.

(57) ABSTRACT

The present invention predicts a timing when there may occur a change in the physical condition of a user. A body condition predicting device (10) includes: a collating section (112) configured to collate biological data acquired by a biosensor (30) with a biological data pattern representing drifting over time of the biological data, the biological data pattern being associated with either or both attribute data and environmental data; and a biological data drifting predicting section (113) configured to predict, based on a result of collation performed by the collating section, the drifting over time of the biological data that occurs after the biosensor (30) acquires the biological data.

13 Claims, 15 Drawing Sheets

(51) Int. Cl.
    *G16H 40/63* (2018.01)
    *G16H 10/40* (2018.01)
    *A61B 5/024* (2006.01)
(52) U.S. Cl.
    CPC ............ *G16H 10/40* (2018.01); *G16H 40/63* (2018.01); *A61B 5/024* (2013.01); *A61B 5/443* (2013.01); *A61B 2560/0242* (2013.01)
(58) Field of Classification Search
    CPC . A61B 2560/0242; G16H 40/63; G06Q 50/22
    USPC ........................................................ 600/301
    See application file for complete search history.

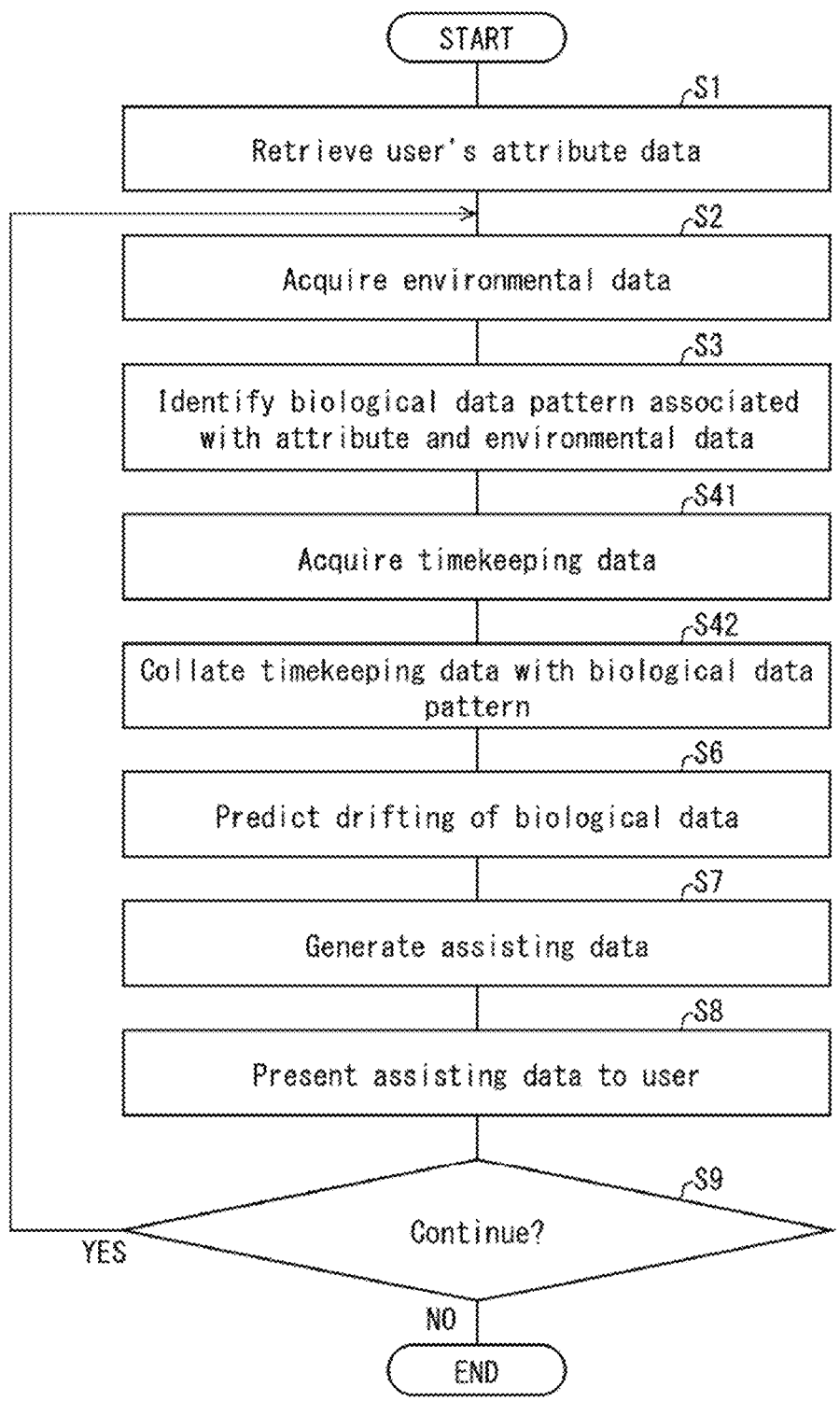

BODY CONDITION PREDICTING DEVICE, METHOD, AND PROGRAM

TECHNICAL FIELD

The following disclosure relates to body condition predicting devices and related technology.

BACKGROUND ART

Recent years have seen development of technology that alerts a user to the possibility of an abnormal change in physical condition before the change actually occurs. An example of such technology is disclosed in Patent Literature 1.

Patent Literature 1 describes a health management system that: analyzes the correlation between the environment and changes in the physical condition of a user on the basis of collected body and environmental information; and collates factor analysis data (i.e., results of analysis) with newly acquired environmental information, in order to predict a change in the physical condition of the user. The health management system then notifies the user of the predicted change in the physical condition. This health management system enables the prediction of a change in physical condition that may occur to a user in the near future and the notification to the user of the prediction before an abnormal change actually happens.

CITATION LIST

Patent Literature

Patent Literature 1: Japanese Unexamined Patent Application Publication, Tokukai, No. 2013-238970 (Publication Date: Nov. 28, 2013)

SUMMARY OF INVENTION

Technical Problem

The health management system described in Patent Literature 1 is capable of predicting changes in physical condition that may occur in the near future, but falls short of specifically determining a timing of such a change. Having received a notice about his/her health condition from the system, the user could still miss an appropriate timing to take preventive measures.

The following disclosure is made in view of this issue and has an object to provide, for example, a body condition predicting device capable of predicting a timing when there may occur a change in the physical condition of the user.

Solution to Problem

To address the issue, the present invention, in an aspect thereof, is directed to a body condition predicting device to be connected in a communicable manner to: a biological data acquisition section configured to acquire biological data representing a condition of a living body; and an environmental data acquisition section configured to acquire environmental data representing a condition of an environment surrounding the living body, the body condition predicting device including: a collating section configured to collate the biological data acquired by the biological data acquisition section with a biological data pattern representing drifting over time of the biological data, the biological data pattern being associated with either or both attribute data representing an attribute of the living body and the environmental data acquired by the environmental data acquisition section; and a predicting section configured to predict, based on a result of collation performed by the collating section, the drifting over time of the biological data that occurs after the biological data acquisition section acquires the biological data.

To address the issue, the present invention, in another aspect thereof, is directed to a method of predicting a body condition, the method including: the biological data acquisition step of acquiring biological data representing a condition of a living body; the environmental data acquisition step of acquiring environmental data representing a condition of an environment surrounding the living body; the collating step of collating the biological data acquired in the biological data acquisition step with a biological data pattern representing drifting over time of the biological data, the biological data pattern being associated with either or both attribute data representing an attribute of the living body and the environmental data acquired in the environmental data acquisition step; and the predicting step of predicting, based on a result of collation performed in the collating step, the drifting over time of the biological data that occurs after the biological data is acquired in the biological data acquisition step.

To address the issue, the present invention, in a further aspect thereof, is directed to a body condition predicting device to be connected in a communicable manner to: a timekeeping section; and an environmental data acquisition section configured to acquire environmental data representing a condition of an environment surrounding a living body, the body condition predicting device including: a collating section configured to collate a current time tracked by the timekeeping section with a biological data pattern representing drifting over time of biological data, the biological data pattern being associated with either or both attribute data representing an attribute of the living body and the environmental data acquired by the environmental data acquisition section; and a predicting section configured to predict, based on a result of collation performed by the collating section, the drifting over time of the biological data that occurs after the current time tracked by the timekeeping section.

Advantageous Effects of Invention

The present invention, in an aspect thereof, results in the advantage of being able to predicting a timing when there may occur a change in the physical condition of the user (living body).

BRIEF DESCRIPTION OF DRAWING

FIG. 15 is a flow chart depicting an example method of predicting biological data in accordance with Embodiment 6.

DESCRIPTION OF EMBODIMENTS

Embodiment 1

An embodiment of the present invention will be described in reference to FIGS. 1 to 3.

User Assisting System 1

Figure 1:
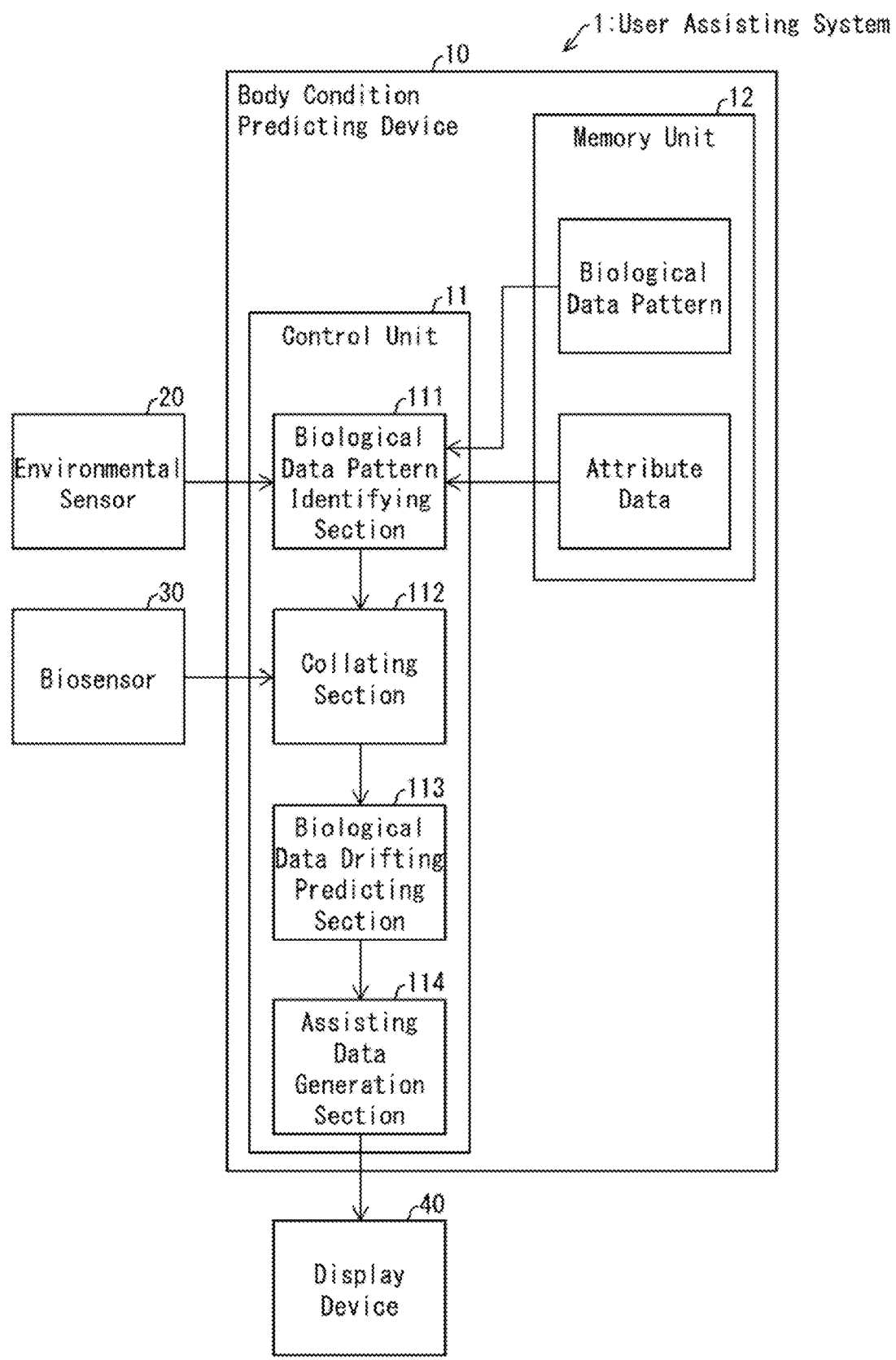
FIG. 1 is a diagram showing an example configuration of a user assisting system in accordance with Embodiment 1.

FIG. 1 is a diagram showing an example configuration of a user assisting system 1 in accordance with the present embodiment. The user assisting system 1 predicts changes in the physical condition of a user (living body) and helps the user manage his/her physical condition on the basis of predicted results. Referring to FIG. 1, the user assisting system 1 includes a body condition predicting device 10, an environmental sensor 20 (environmental data acquisition section), a biosensor 30 (biological data acquisition section), and a display device 40. The body condition predicting device 10 is connected in a communicable manner to the environmental sensor 20, the biosensor 30, and the display device 40. The body condition predicting device 10 will be described later in more detail.

The environmental sensor 20 acquires data representing at least either one or both of the temperature and humidity of the environment surrounding the user as environmental data for transmission to the body condition predicting device 10. The environmental sensor 20 in accordance with the present embodiment may be, for example, a temperature sensor or a humidity sensor. Alternatively, the environmental sensor 20 may be a UV (ultraviolet) sensor that measures the intensity of ultraviolet light shining on the user or an illuminance sensor that measures the illuminance of light shining on the user. The following description will assume that the environmental sensor 20 is a temperature sensor.

The body condition predicting device 10 may alternatively be connected to a receiver (environmental data acquisition section) (not shown) capable of acquiring environmental data, instead of being connected to the environmental sensor 20. The receiver acquires environmental data from an external device containing environmental data. The environmental data may be, for example, weather information for the environment surrounding the user (user's geographical location). The receiver acquires environmental data from the external device over a network.

The biosensor 30 acquires biological data representing a condition of the user. The biosensor 30 acquires data representing, for example, the user's skin surface water content, body temperature, or heart rate (pulse wave) as biological data. In other words, the biosensor 30 may be a perspiration level sensor for measuring the user's skin surface water content, a clinical thermometer for measuring the user's body temperature, or a pulse rate meter for measuring the user's heart rate. The present embodiment assumes that the biosensor 30 is a perspiration level sensor.

The display device 40 displays assisting data that is generated by the body condition predicting device 10 to indicate a measure that reduces the possibility of a changes occurring in the physical condition of the user. The user assisting system 1 simply needs to include a presentation section capable of presenting the content of the assisting data to the user. The display device 40, as a presentation section, may be replaced with, for example, a speaker for outputting the content in sound.

Configuration of Body Condition Predicting Device

Next, a description will be given of the body condition predicting device 10 in reference to FIGS. 1 and 2. The body condition predicting device 10 predicts a condition of the user and includes a control unit 11 and a memory unit 12 as shown in FIG. 1.

The control unit 11 controls the overall operation of the body condition predicting device 10 and includes a biological data pattern identifying section 111 (identifying section), a collating section 112, a biological data drifting predicting section 113 (predicting section), and an assisting data generation section 114. A specific configuration of the control unit 11 will be described later in detail.

The memory unit 12 contains, for example, various control programs executed by the control unit 11 and is built, for example, around a hard disk, a flash memory, or a like non-volatile storage device. The memory unit 12, as an example, contains biological data patterns at least one of which is to be identified by the biological data pattern identifying section 111 and also contains attribute data referenced when identifying a biological data pattern. Attribute data represents the user's attribute(s) including at least one of the user's physique, age, and gender. The user's physique is an attribute related to the physical condition of the user such as the user's height, weight, or body fat percentage. Biological data patterns will be described later in more detail.

The biological data patterns and attribute data are not necessarily stored in the memory unit 12 in advance and only need to exist when the biological data pattern identifying section 111 identifies a biological data pattern. The biological data patterns and attribute data may be, for example, inputted, when the biological data pattern identifying section 111 identifies a biological data pattern, via an input section (not shown) through which the user can manually input commands and data.

Configuration of Control Unit

The biological data pattern identifying section 111 identifies a biological data pattern for use in collation by the collating section 112 of the biological data acquired by the biosensor 30. A biological data pattern represents drifting of biological data over time. Biological data patterns in the present embodiment represent the drifting of the perspiration level of the user over time.

Specifically, the biological data pattern identifying section 111 identifies one of biological data patterns associated with attribute values representing predetermined attributes of the user, the one of biological data patterns corresponding to the attribute data stored in the memory unit 12. The biological data pattern identifying section 111 also identifies one of biological data patterns associated with predetermined environmental values representing prescribed environmental conditions, the one of biological data patterns corresponding to the environmental data acquired by the environmental sensor 20.

More specifically, (1) if there are prepared biological data patterns associated only with attribute values, the biological data pattern identifying section 111 identifies one of the biological data patterns that corresponds to the attribute data using only the attribute data. (2) If there are prepared biological data patterns associated only with environmental values, the biological data pattern identifying section 111 identifies one of the biological data patterns that corresponds to the environmental data using only the environmental data. (3) If there are prepared biological data patterns associated with both attribute values and environmental values, the biological data pattern identifying section 111 identifies one of the biological data patterns that corresponds to the attribute and environmental data using both the attribute data and the environmental data. The present embodiment is described assuming case (3).

Figure 2:
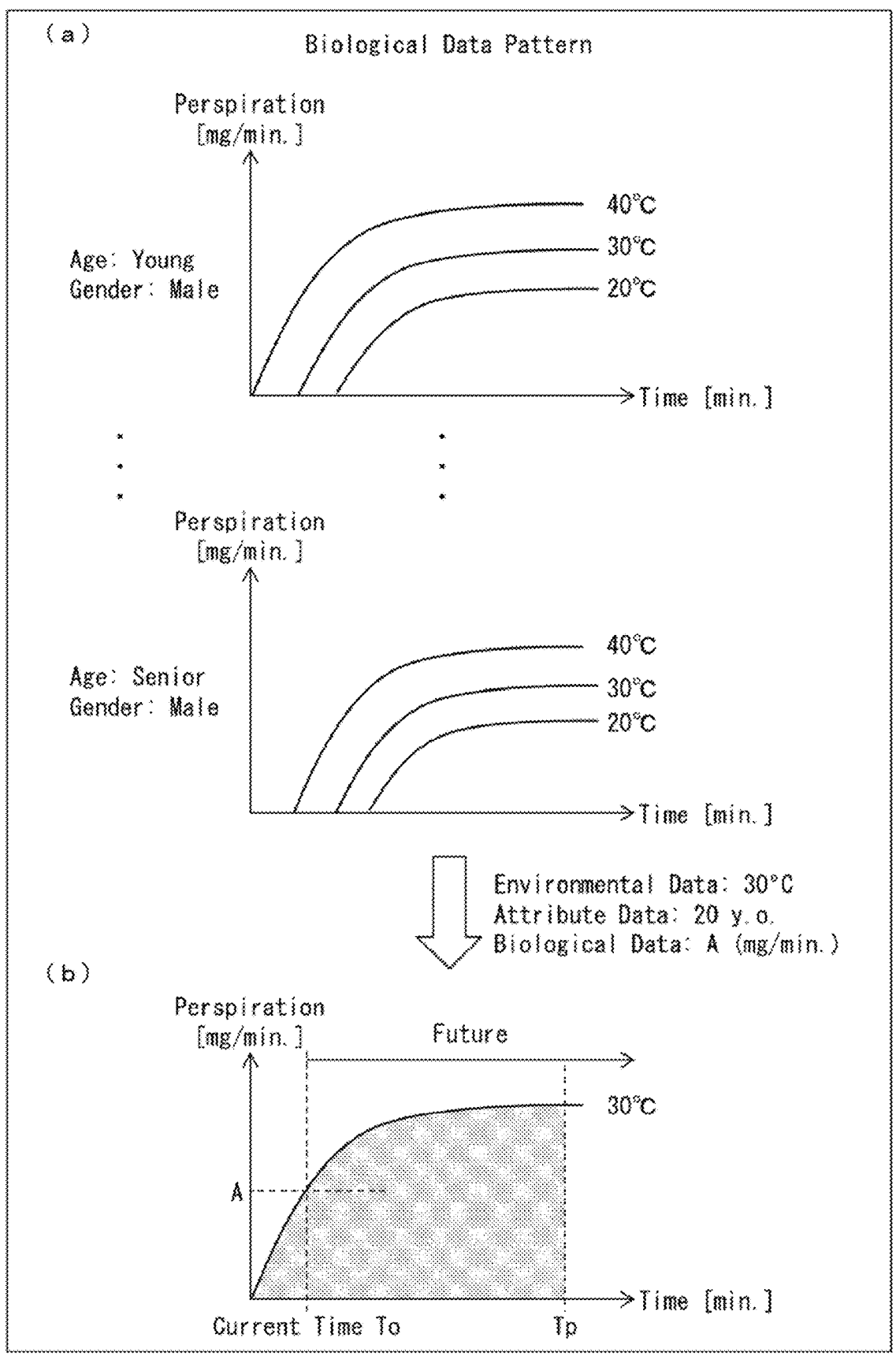
FIG. 2 is a set of diagrams showing example biological data patterns, (a) of FIG. 2 showing example biological data patterns stored in a memory unit and (b) of FIG. 2 showing an example biological data pattern identified by a biological data pattern identifying section.

An example biological data pattern identified by the biological data pattern identifying section 111 is now described in reference to FIG. 2. FIG. 2 is a set of diagrams showing example biological data patterns, (a) of FIG. 2 showing example biological data patterns stored in the memory unit 12 and (b) of FIG. 2 showing an example biological data pattern identified by the biological data pattern identifying section 111.

Referring to (a) of FIG. 2, the memory unit 12 contains a plurality of biological data patterns associated respectively with a plurality of predetermined temperatures (environmental values). In the example shown in (a) of FIG. 2, there are prepared biological data patterns for temperatures of 20° C., 30° C., and 40° C. Needless to say, there may be prepared a plurality of biological data patterns for other temperatures. In addition, the biological data pattern identifying section 111 may generate (interpolate or extrapolate) missing biological data patterns from available biological data patterns.

Still referring to (a) of FIG. 2, there are prepared a plurality of biological data patterns associated with a plurality of attribute values representing predetermined user ages and genders. In the example shown in (a) of FIG. 2, there are prepared a plurality of biological data patterns associated respectively with a plurality of attribute values (e.g., from 10 to 19 years of age and from 20 to 29 years of age) for an attribute, "age." For another attribute, "gender," there are prepared biological data patterns associated with an attribute value, "male."

There may be prepared biological data patterns associated with an attribute value, "female," for the attribute, "gender." The biological data patterns are not necessarily associated with attribute values for a plurality of attributes and may be associated with attribute values for only one attribute (e.g., age).

Referring now to (b) of FIG. 2, when the environmental sensor 20 has acquired environmental data that indicates a temperature of 30° C. and the memory unit 12 contains attribute data that indicates 20 years of age and the male gender, as an example, the biological data pattern identifying section 111 identifies a biological data pattern that corresponds to these values.

The memory unit 12 pre-stores biological data patterns in the present embodiment. The biological data pattern identifying section 111 identifies one of these biological data patterns using the attribute and environmental data. Alternatively, there may be prepared no biological data patterns in advance. In such a case, there is prepared an equation for generating biological data patterns in the memory unit 12. The biological data pattern identifying section 111 may identify a biological data pattern for use by the collating section 112, by plugging the values of the attribute and/or environmental data into the equation.

The collating section 112 collates the biological data acquired by the biosensor 30 with the biological data pattern identified by the biological data pattern identifying section 111. Accordingly, the biological data pattern used in collation in the present embodiment is associated with both the attribute data and the environmental data and, as described earlier, may be associated only with the attribute data or only with the environmental data.

More specifically, the collating section 112 acquires, from the biosensor 30, the biological data acquired by the biosensor 30 and determines a time that corresponds to a value of the biological data (value A in (b) of FIG. 2) on the identified biological data pattern. Then, as shown in (b) of FIG. 2, the collating section 112 designates this particular time (i.e., a time corresponding to value A of the biological data on the biological data pattern) as current time To. The graph representing the biological data pattern has a horizontal axis that represents a time elapsed from the start of measurement of the biological data indicated by the biological data pattern. Therefore, current time To is a point in time that comes after the start of the measurement.

The biological data drifting predicting section 113 predicts, on the basis of a result of the collation performed by the collating section 112, the drifting over time of the biological data that will occur after the biosensor 30 acquires the biological data, that is, after current time To shown in (b) of FIG. 2 (i.e., in the future with respect to current time To). As an example, the biological data drifting predicting section 113 predicts, from the identified biological data pattern, perspiration will (1) reach what level in how many minutes from current time To and (2) reach a prescribed perspiration level (prescribed level) in how many minutes (approximately when the prescribed perspiration level will be reached).

The perspiration level that is to be compared with a prescribed perspiration level may be a perspiration rate per unit time (e.g., perspiration rate per minute) indicated by the biological data pattern or may be a cumulative amount of perspiration since time 0 on the biological data pattern. The cumulative amount may be calculated as the size of an area enclosed by a time axis (horizontal axis, y=0), prescribed time T (x=T), and a curve representing the perspiration level in a graph representing the temporal characteristics of the perspiration level. In the example shown in (b) of FIG. 2, the cumulative amount up to time Tp is calculated as the size of the dotted area surrounded by the time axis, time Tp, and the curve representing the perspiration level.

An abnormal change could generally occur in physical condition if the water content of the human body decreases by a prescribed amount. Specifically, if the water lost by the human body (dehydration level) is equal to 2% or less of the body weight, the user may only feel thirsty. If the dehydration level is equal to 2% or more, particularly in the range of approximately 3 to 4%, the user may lose appetite, be fatigued, or otherwise experience an abnormal change in his/her body. If the dehydration level is equal to 5% or more of the body weight, the user may find it difficult to speak normally, experience cramps, or otherwise suffer a serious, abnormal change.

In view of these facts, the body condition predicting device 10, if it is acquiring the user weight as an attribute, designates the amount of water equal to 2% of the body weight of the user as a threshold as an example. The biological data drifting predicting section 113 calculates the cumulative amount of perspiration from time 0 to a given time on the identified biological data pattern (size of the area described above) and then determines time Tp at which the cumulative amount reaches the threshold (see (b) of FIG. 2). In other words, the biological data drifting predicting section 113 is capable of predicting that if the user remains in the current environment (at 30° C. in the example shown in FIG. 2), the user will experience an abnormal change in his/her physical condition in Tp-To minutes.

The assisting data generation section 114 generates assisting data on the basis of the drifting over time of the biological data that is predicted by the biological data drifting predicting section 113, for display on the display device 40. The content of the assisting data generated by the assisting data generation section 114 may be, for example, a notification of a timing when there will be an increased risk of heatstroke or when the user should drink water.

As an example, if the biological data drifting predicting section 113 has predicted that there will be an abnormal change in the user's physical condition in Tp-To minutes, the assisting data generation section 114 generates assisting data representing a content, "You may suffer heatstroke in Tp-To minutes. You are advised to drink sufficient water before that."

Method of Predicting Body Condition

Next, a description will be given of a method of predicting biological data in reference to FIG. 3. FIG. 3 is a flow chart depicting an example method of predicting biological data (method of controlling the body condition predicting device 10 and related devices/units/sections) in accordance with the present embodiment.

Figure 3:
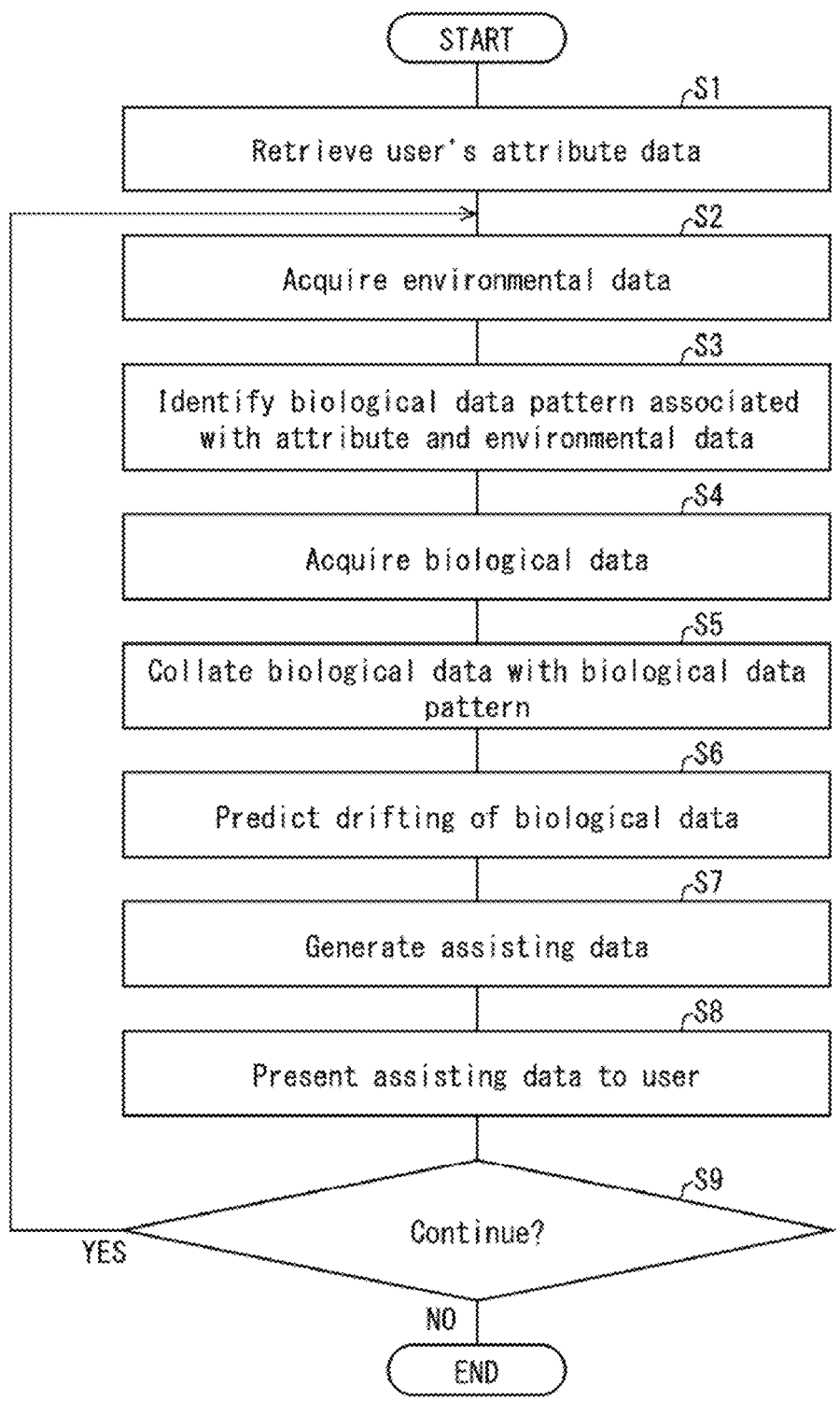
FIG. 3 is a flow chart depicting an example method of predicting biological data in accordance with Embodiments 1, 2, and 4.

Referring to FIG. 3, the biological data pattern identifying section 111 retrieves the user's attribute data from the memory unit 12 (S1). Then, the environmental sensor 20 acquires environmental data, and the biological data pattern identifying section 111 acquires this environmental data from the environmental sensor 20 (S2: the environmental data acquisition step). The environmental sensor 20 may, for example, acquire environmental data and transmit the acquired environmental data to the biological data pattern identifying section 111 in response to a request from the biological data pattern identifying section 111. Alternatively, the environmental sensor 20 may selectively transmit the latest set of environmental data collected prior to such a request to the biological data pattern identifying section 111.

The biological data pattern identifying section 111 identifies, as a biological data pattern for use by the collating section 112, a biological data pattern associated with both the retrieved attribute data and the environmental data acquired from the environmental sensor 20 out of a plurality of biological data patterns stored in the memory unit 12 (S3).

Next, the biosensor 30 acquires biological data (S4: the biological data acquisition step). The collating section 112 then acquires this biological data from the biosensor 30. The biosensor 30, similarly to the environmental sensor 20, may, for example, acquire biological data in response to a request from the collating section 112 and transmit the acquired biological data to the collating section 112. Alternatively, the biosensor 30 may selectively transmit the latest set of biological data collected prior to such a request to the collating section 112. The collating section 112 collates the acquired biological data with the identified biological data pattern and transmits results of the collation (e.g., a curve and current time To shown in (b) of FIG. 2) to the biological data drifting predicting section 113 (S5: the collating step).

The biological data drifting predicting section 113 predicts drifting over time of the biological data that will occur after the acquisition of the biological data on the basis of the results of the collation and transmits results of the prediction to the assisting data generation section 114 (S6: the predicting step). The assisting data generation section 114 generates assisting data on the basis of the results of the prediction (S7), for display on the display device 40 (S8). As an example, the control unit 11 returns the process to S2 if S2 to S8 are to be carried out in response to a user command (YES in S9) and ends the process if these steps are not to be carried out in response to a user command (NO in S9).

S2 and S3 may be carried out simultaneously with S4 or after S4.

Major Effects

The body condition predicting device 10 is capable of predicting drifting over time of biological data that will occur after the acquisition of the biological data by collating the biological data acquired by the biosensor 30 with the biological data pattern identified by the biological data pattern identifying section 111. The body condition predicting device 10 can thus predict how soon from the acquisition of biological data a value indicated by the biological data will reach approximately what level. It is hence possible to predict a timing when there may occur a change in the physical condition of the user.

Whether the biological data pattern used in the collation is helpful or not to appropriately understand the user's current health condition depends on the user's current attributes (values indicated by attribute data) and/or the environment surrounding the user (values indicated by environmental data). Since the body condition predicting device 10 collates the acquired biological data with the biological data pattern associated with attribute data and/or environmental data, it is possible to make the prediction in accordance with differences between individual users and/or different environmental conditions surrounding the users.

The body condition predicting device 10 generates assisting data on the basis of the prediction and presents the assisting data to the user. In other words, the body condition predicting device 10 is capable of notifying the user of a timing when there will be a high possibility of a health problem such as poor physical condition before the problem actually occurs. That enables the user to take preventive measures at a suitable time to avoid such a change occurring in his/her physical condition.

Variation Examples

As described earlier, the environmental sensor 20 is not necessarily a temperature sensor and may be, for example, a humidity sensor, a UV sensor, or an illuminance sensor. If the environmental sensor 20 is a humidity sensor, the biological data patterns represent temporal changes in perspiration for different humidity levels. If the environmental sensor 20 is a UV sensor, the biological data patterns represent temporal changes in perspiration for different intensity levels of ultraviolet light. If the environmental sensor 20 is an illuminance sensor, the biological data patterns represent temporal changes in perspiration for different illuminance levels.

As described earlier, the biosensor 30 is not necessarily a perspiration level sensor and may be, for example, a clinical thermometer or a pulse rate meter. If the biosensor 30 is a clinical thermometer, the biological data patterns represent temporal changes in body temperature. If the biosensor 30 is a pulse rate meter, the biological data patterns represent temporal changes in heart rate. In these cases, the body condition predicting device 10 can provide the user with information that, for example, there will be a risk of heatstroke at a prescribed time when the body temperature or heart rate reaches a prescribed level following the acquisition of biological data.

The biosensor 30 may be a combination of these different types of sensors. In other words, the biological data may represent at least any one of the skin surface water content, body temperature, and heart rate of the user. As an example, if the biosensor 30 is a combination of a perspiration level sensor and a clinical thermometer, the memory unit 12 contains (1) biological data patterns representing drifting over time of perspiration associated with attribute values and/or environmental values and (2) biological data patterns representing drifting over time of body temperature associated with attribute values and/or environmental values.

Using this biological data, the biological data drifting predicting section 113 then predicts a timing when there may occur an abnormal change in the user's physical condition as described earlier. If the predicted timing varies with the perspiration level and body temperature, the biological data drifting predicting section 113 may (1) designate an earlier one of two predicted timings as the result of the prediction or (2) designate another timing obtained by a prescribed computation, such as an average value of the two timings, as the result of the prediction.

As described here, the drifting over time of biological data of the user that will occur after the acquisition of the biological data can be predicted using a combination of different types of biosensors 30. This configuration provides additional parameters available for use in the prediction over the configuration where a single biosensor 30 is used. It is hence possible to predict, from various perspectives, a timing when there may occur a change in physical condition, which will likely improve accuracy of the prediction.

Embodiment 2

Another embodiment of the present invention will be described in reference to FIGS. 3 to 6. For convenience of description, members of the present embodiment that have the same function as members of the previous embodiment are indicated by the same reference numerals, and description thereof is omitted.

Configuration of Body Condition Predicting Device

Figure 4:
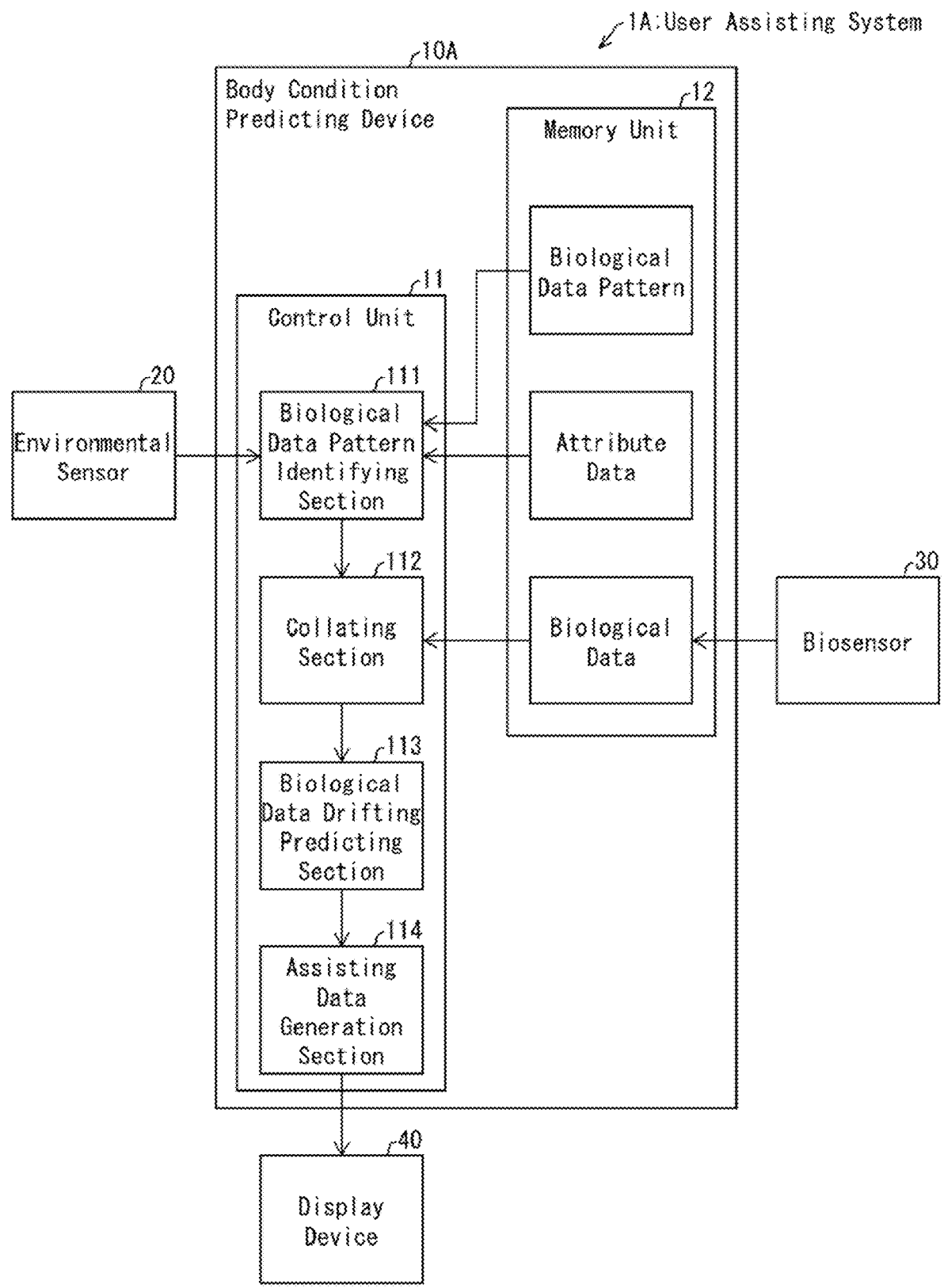
FIG. 4 is a diagram showing an example configuration of a user assisting system in accordance with Embodiment 2.

First, a description will be given of an example body condition predicting device 10A in accordance with the present embodiment in reference to FIG. 4. FIG. 4 is a diagram showing an example configuration of a user assisting system 1A in accordance with the present embodiment. The user assisting system 1A differs from the user assisting system 1 of Embodiment 1 in that it includes the body condition predicting device 10A.

Specifically, in the body condition predicting device 10 of Embodiment 1, the collating section 112 acquires the biological data acquired by the biosensor 30 and collates the biological data with a biological data pattern identified by the biological data pattern identifying section 111. In contrast, in the body condition predicting device 10A of the present embodiment, the biosensor 30 acquires biological data at a plurality of times, and the collating section 112 uses a plurality of sets of biological data acquired by the biosensor 30 in collation.

More specifically, in the body condition predicting device 10A, the memory unit 12 temporarily stores the biological data acquired by the biosensor 30 at a plurality of times. The collating section 112 calculates an approximation curve (a temporal property derived from a plurality of sets of biological data) by, for example, applying a least square technique on a plurality of sets of biological data acquired by the biosensor 30 at a plurality of times. The collating section 112 then collates the calculated approximation curve with the biological data pattern identified by the biological data pattern identifying section 111 (fits the calculated approximation curve to the biological data pattern identified by the biological data pattern identifying section 111).

The collating section 112, as an example, designates the latest time on the approximation curve obtained by fitting to the biological data pattern as current time To. Current time To is not necessarily determined by this method. Alternatively, current time To may be determined, for example, by designating the earliest time on the approximation curve obtained by fitting to the biological data pattern as current time To or by designating the time at which the approximation curve best fits to the biological data pattern (time when the match level is highest) as current time To.

The collating section 112 does not necessarily calculate an approximation curve from a plurality of sets of biological data and use the approximation curve in collation. As an alternative example, the collating section 112 may calculate an average value of the perspiration levels represented by a plurality of sets of biological data and use the calculated average value in collation.

Method of Predicting Body Condition

Next, a description will be given of a method of predicting biological data in reference to FIG. 3. S1 to S3, S6, and the subsequent steps in FIG. 3 are the same as those in Embodiment 1, and description of these steps is omitted.

In S4 in FIG. 3, the biosensor 30 acquires biological data at a plurality of times, and the body condition predicting device 10A stores this plurality of sets of biological data in the memory unit 12. The collating section 112 acquires the plurality of sets of biological data from the memory unit 12 and, for example, calculates an approximation curve. Then, in S5, the collating section 112 fits the calculated approximation curve to a biological data pattern identified by the biological data pattern identifying section 111, in order to determine, on the biological data pattern, current time To at which the biological data is acquired. This is followed by temporal prediction of biological data and generation of assisting data.

Major Effects

The values indicated by the biological data acquired by the biosensor 30 may have a measurement error, for example, due to manufacturing variations of the biosensor 30. If a value indicated by a single set of biological data has a measurement error and is used in collation, the determination of current time To may also be affected by the measurement error.

Since the body condition predicting device 10A uses, in collation, the biological data acquired at a plurality of times, the body condition predicting device 10A is capable of restraining the measurement error from affecting the determination of current time To. The body condition predicting device 10A is therefore capable of more accurately determining current time To even when the acquired biological data has irregularities. The body condition predicting device 10A is hence capable of more accurately predicting drifting over time of the biological data (e.g., a timing when there may occur a change in physical condition).

Variation Examples

Figure 5:
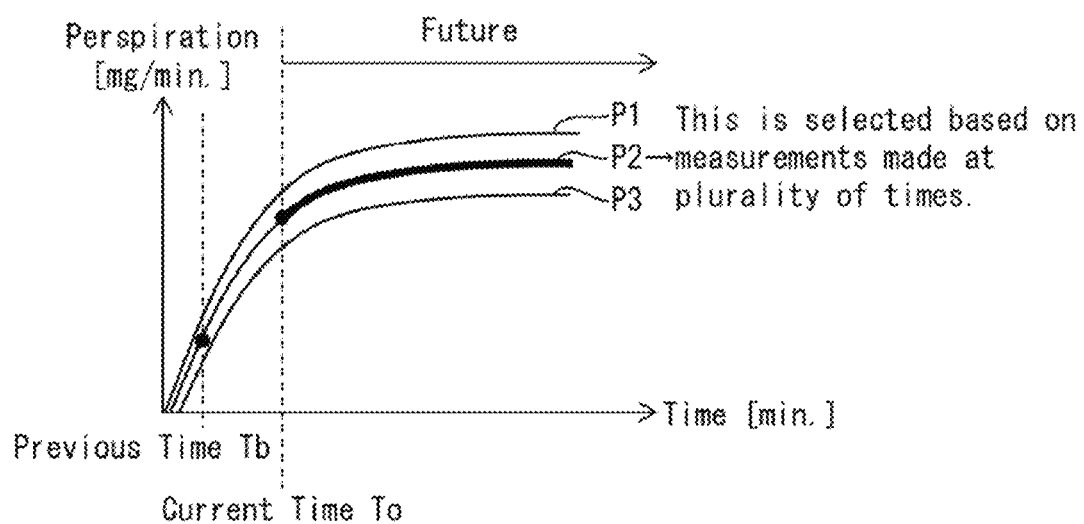
FIG. 5 is a diagram showing an example set of biological data patterns one of which has been identified by a biological data pattern identifying section.
Figure 6:
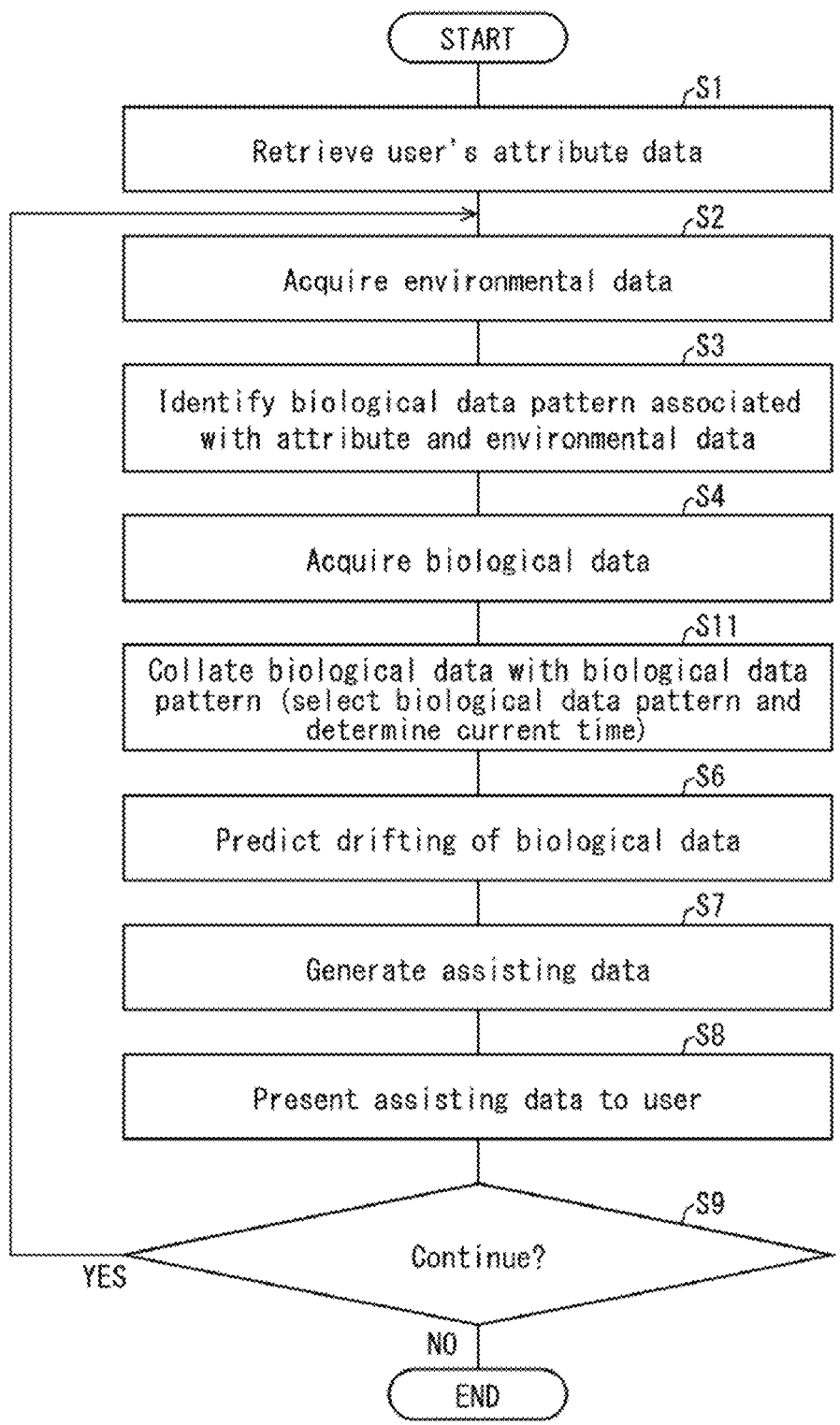
FIG. 6 is a flow chart depicting an example method of predicting biological data in accordance with a variation example of Embodiment 2.

Variation examples of Embodiment 2 will be described in reference to FIGS. 4 to 6. FIG. 5 is a diagram showing an example set of biological data patterns one of which has been identified by the biological data pattern identifying section 111. FIG. 6 is a flow chart depicting an example method of predicting biological data in accordance with a variation example of Embodiment 2.

Configuration of Body Condition Predicting Device

Similarly to the previous embodiment, the collation is done using a plurality of sets of biological data acquired by the biosensor 30 at a plurality of times in the present variation example. The present variation example, however, differs from the body condition predicting device 10A of Embodiment 2 in that the present variation example involves an additional process detailed below. The collating section 112 selects one of the identified biological data patterns using the plurality of sets of biological data acquired by the biosensor 30. The biological data drifting predicting section 113 then predicts drifting over time of the biological data using the biological data pattern selected by the collating section 112.

More specifically, the biological data pattern identifying section 111 identifies, among those biological data patterns stored in the memory unit 12, a plurality of biological data patterns associated with a value indicated by the acquired attribute data and a value indicated by the acquired environmental data. FIG. 5 shows an example where three biological data patterns P1, P2, and P3 have been identified. The biological data pattern identifying section 111 identifies these biological data patterns, for example, in the following manner.

The biological data pattern identifying section 111 identifies a single biological data pattern associated with attribute data and environmental data as in Embodiment 1. If the biological data pattern identifying section 111 cannot identify a biological data pattern associated with attribute data and environmental data, the biological data pattern identifying section 111 identifies a single biological data pattern through interpolation or extrapolation as in Embodiment 1.

Thereafter, the biological data pattern identifying section 111 identifies a plurality of biological data patterns (two biological data pattern if three biological data patterns are to be identified) having similar properties to those of the identified one of the biological data patterns. If the biological data pattern identifying section 111 cannot identify any biological data patterns having similar properties, the biological data pattern identifying section 111 generates such biological data patterns through interpolation or extrapolation that satisfies prescribed requirements. In other words, the biological data pattern identifying section 111 identifies biological data patterns associated with an attribute value that falls in a prescribed range that includes a value indicated by the attribute data and/or an environmental value that falls in a prescribed range that includes a value indicated by the environmental data. For example, when the acquired attribute data indicates an age of 20 years and the acquired environmental data indicates a temperature of 30° C., the biological data pattern identifying section 111 generates biological data patterns for a temperature of 29.9° C. or 30.1° C.

Using the plurality of sets of biological data acquired by the biosensor 30 at a plurality of times, the collating section 112 selects one of the biological data patterns identified by the biological data pattern identifying section 111. More specifically, as described earlier, the collating section 112 collates an approximation curve calculated from the plurality of sets of biological data with the biological data patterns identified by the biological data pattern identifying section 111 and selects one of the biological data patterns that shows the highest match level as the biological data pattern for the biological data drifting predicting section 113 to use in prediction. The collating section 112 also determines current time To for the selected biological data pattern.

The biological data drifting predicting section 113 predicts drifting over time of the biological data of the user using the biological data pattern selected by the collating section 112 and current time To determined by the collating section 112. In the example shown in FIG. 5, the collating section 112 calculates an approximation curve for the biological data at a plurality of times including previous time Tb and current time To and selects the biological data pattern P2, which has the highest match level for the approximation curve. The biological data drifting predicting section 113 then predicts the drifting over time of the biological data of the user that will occur after the acquisition of the biological data (after current time To, indicated by a thick line in FIG. 5).

Method of Predicting Body Condition

Next, a description will be given of a method of predicting biological data in reference to FIG. 6. FIG. 6 is a flow chart depicting an example method of predicting biological data in accordance with the present variation example. S1, S2, S4, S6, and the subsequent steps in FIG. 6 are the same as those in Embodiment 1 or 2, and description of these steps is omitted.

In the present variation example, as described earlier, in step S3 in FIG. 6, the biological data pattern identifying section 111 identifies, among those biological data patterns stored in the memory unit 12, a plurality of biological data patterns from which the collating section 112 is to select a biological data pattern. The collating section 112 acquires the plurality of sets of biological data acquired by the biosensor 30 at a plurality of times in step S4. Then in step S11, the collating section 112 calculates an approximation curve for the sets of biological data, fits the approximation curve to the biological data patterns identified by the biological data pattern identifying section 111, and selects one of the biological data patterns (collating step). The collating section 112 then determines, on the selected one of the biological data patterns, current time To at which the biological data is acquired. This is followed by temporal prediction of biological data and generation of assisting data.

Major Effects

The biological data pattern identifying section 111 identifies a plurality of biological data patterns associated with the acquired attribute and environmental data as described above. The collating section 112 can thereby select a biological data pattern that is more suited to the user's condition (current, actual condition). It is hence possible to more accurately predict the drifting over time of the biological data.

Embodiment 3

Figure 7:
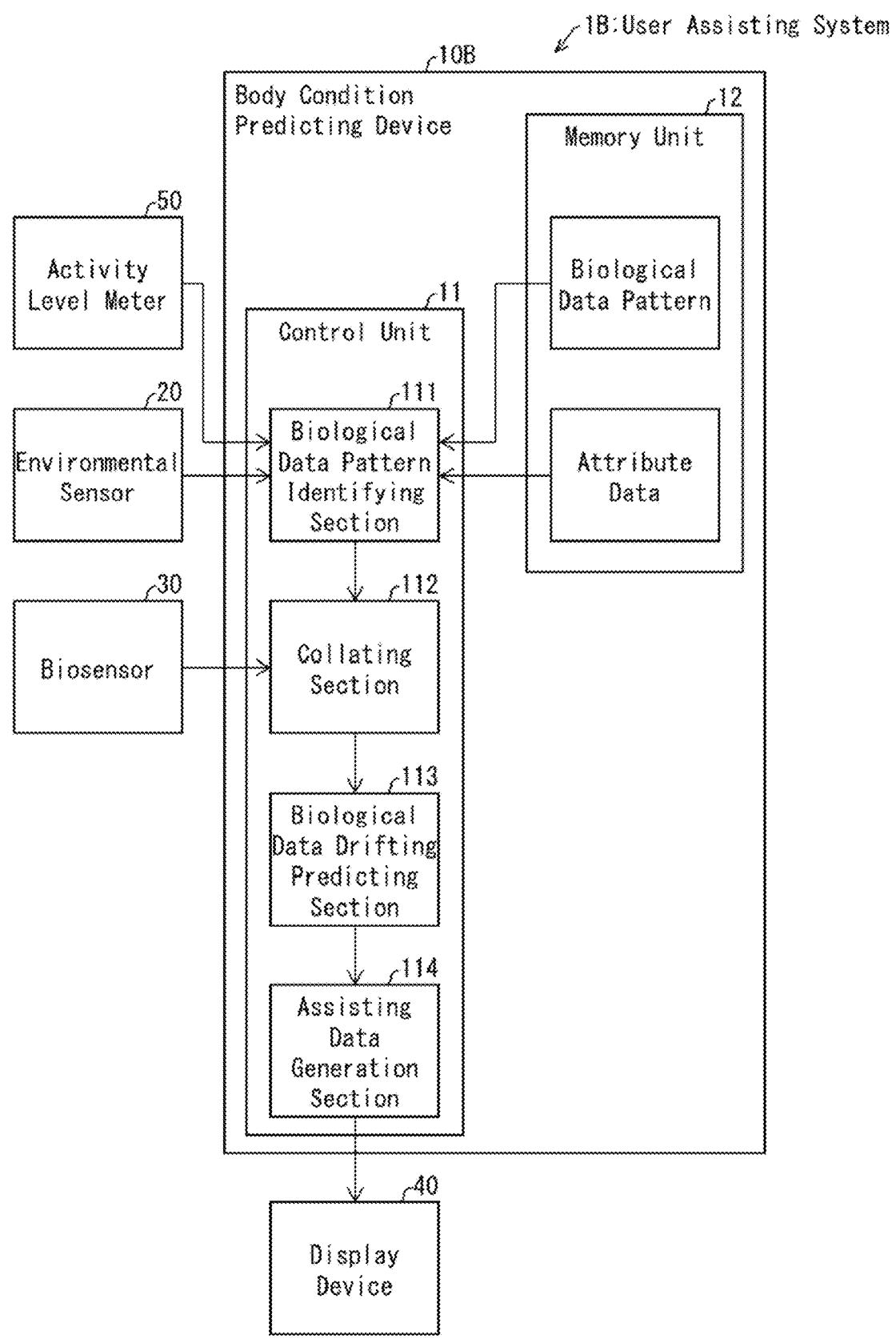
FIG. 7 is a diagram showing an example configuration of a user assisting system in accordance with Embodiment 3.

Another embodiment of the present invention will be described in reference to FIGS. 7 to 9. For convenience of description, members of the present embodiment that have the same function as members of any previous embodiment are indicated by the same reference numerals, and description thereof is omitted.

Configuration of Body Condition Predicting Device

First, a description will be given of an example body condition predicting device 10B in accordance with the present embodiment in reference to FIG. 7. FIG. 7 is a diagram showing an example configuration of a user assisting system 1B in accordance with the present embodiment. The user assisting system 1B differs from the user assisting system 1 of Embodiment 1 in that it includes the body condition predicting device 10B and an activity level meter 50 (activity data acquisition section).

The activity level meter 50 is connected in a communicable manner to the body condition predicting device 10B and acquires activity data representing the activity condition of the user. The activity level meter 50 transmits the acquired activity data to the body condition predicting device 10B.

The activity level meter 50 includes a built-in acceleration sensor and calculates, for example, the physical activity level or calorie consumption of the user on the basis of the acceleration caused by motions of the user that are detected by the acceleration sensor. The activity level meter 50 converts the physical activity level, calorie consumption, and like parameter to METs (metabolic equivalents) in the present embodiment to calculate METs as activity data. An MET is an indicator of the intensity of a physical activity (activity level).

The MET indicates the activity level of a living body by means of energy consumption ratio as compared with the energy consumption at rest (energy consumption at rest=1). Accordingly, a greater MET value can be interpreted into the user being involved in a more vigorous motion.

The activity data acquisition section, which acquires activity data, is not necessarily the activity level meter 50 and may be, for example, a pedometer. A pedometer calculates, for example, a walking speed or a time taken to walk one step on the basis of the acceleration detected by the built-in acceleration sensor of the pedometer. The pedometer then converts the walking speed or time taken to walk one step to an MET to acquire activity data. In other words, the activity data acquisition section needs only to include a sensor (e.g., acceleration sensor) capable of detecting the motion of the user and be configured to acquire activity data.

The present embodiment is described by taking the MET as an example of the activity data. Alternatively, the activity data may be any data representing, for example, the physical activity level or calorie consumption of the user acquired by the activity level meter 50 or the walking speed or time taken to walk one step acquired by a pedometer. METs may be calculated by the biological data pattern identifying section 111. In such cases, these types of data acquired by the activity level meter 50 or the pedometer are transmitted to the biological data pattern identifying section 111.

The activity level meter 50 may include, for example, a built-in pulse rate meter or heart rate meter, as well as an acceleration sensor, and acquire measurements from such a meter as the activity data. If the activity level meter 50 includes a built-in pulse rate meter or heart rate meter, the activity level meter 50 can double as a biosensor that acquires measurements from such a meter as biological data.

In the body condition predicting device 10B, the biological data patterns stored in the memory unit 12 are associated not only with environmental values and/or attribute values, but also with a plurality of predetermined activity values indicating the activity condition of the user (METs indicating the activity level in the present embodiment).

Figure 8:
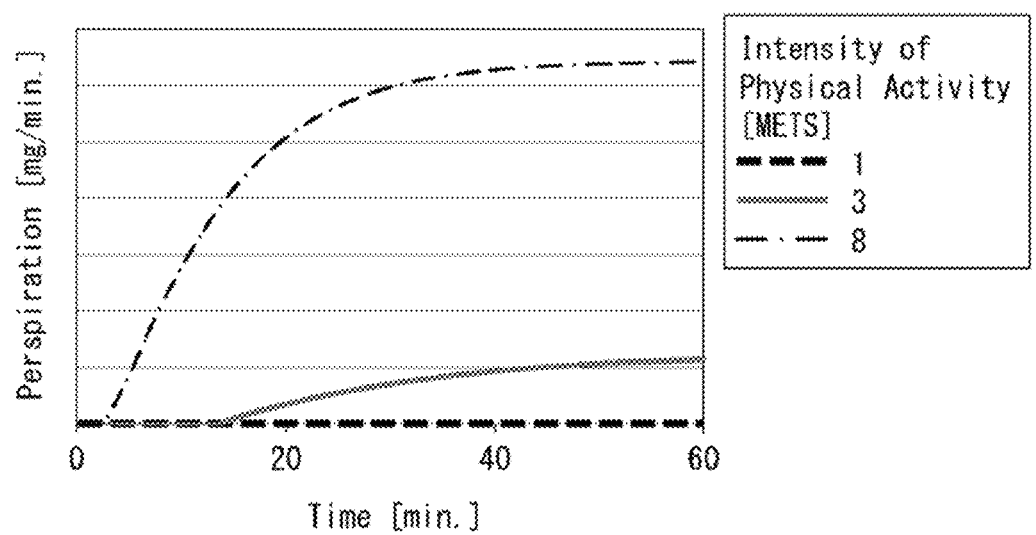
FIG. 8 is a diagram showing an example set of biological data patterns for different activity levels of a user.

FIG. 8 is a diagram showing an example set of biological data patterns for different activity levels of a user. FIG. 8 shows temporal changes in perspiration for different MET values (MET=1, 3, and 8) as example biological data patterns. As can be understand from FIG. 8, the greater the MET value, the more the user perspires. The user's activity level is correlated to his/her perspiration in this manner. The memory unit 12 contains biological data patterns like those shown in FIG. 8 for various attribute values (e.g., ages) and/or environmental values (e.g., temperatures).

The biological data pattern identifying section 111 identifies one of the biological data patterns associated additionally with the activity values for use in collation by the collating section 112, by additionally using the activity data acquired by the activity level meter 50. Accordingly, the collating section 112 uses, in collation, biological data patterns that are associated additionally with the activity data acquired by the activity level meter 50.

Similarly to Embodiment 1, the memory unit 12 may contain an equation for calculating biological data patterns. In such a case, the biological data pattern identifying section 111 identifies a biological data pattern for use by the collating section 112, by plugging the values of the attribute and/or environmental data and the value of the activity data into the equation.

Method of Predicting Body Condition

Next, a description will be given of a method of predicting biological data in reference to FIG. 9. FIG. 9 is a flow chart depicting an example method of predicting biological data in accordance with the present embodiment. S1, S2, S4, and the subsequent steps in FIG. 9 are the same as those in Embodiment 1, and description of these steps is omitted.

Figure 9:
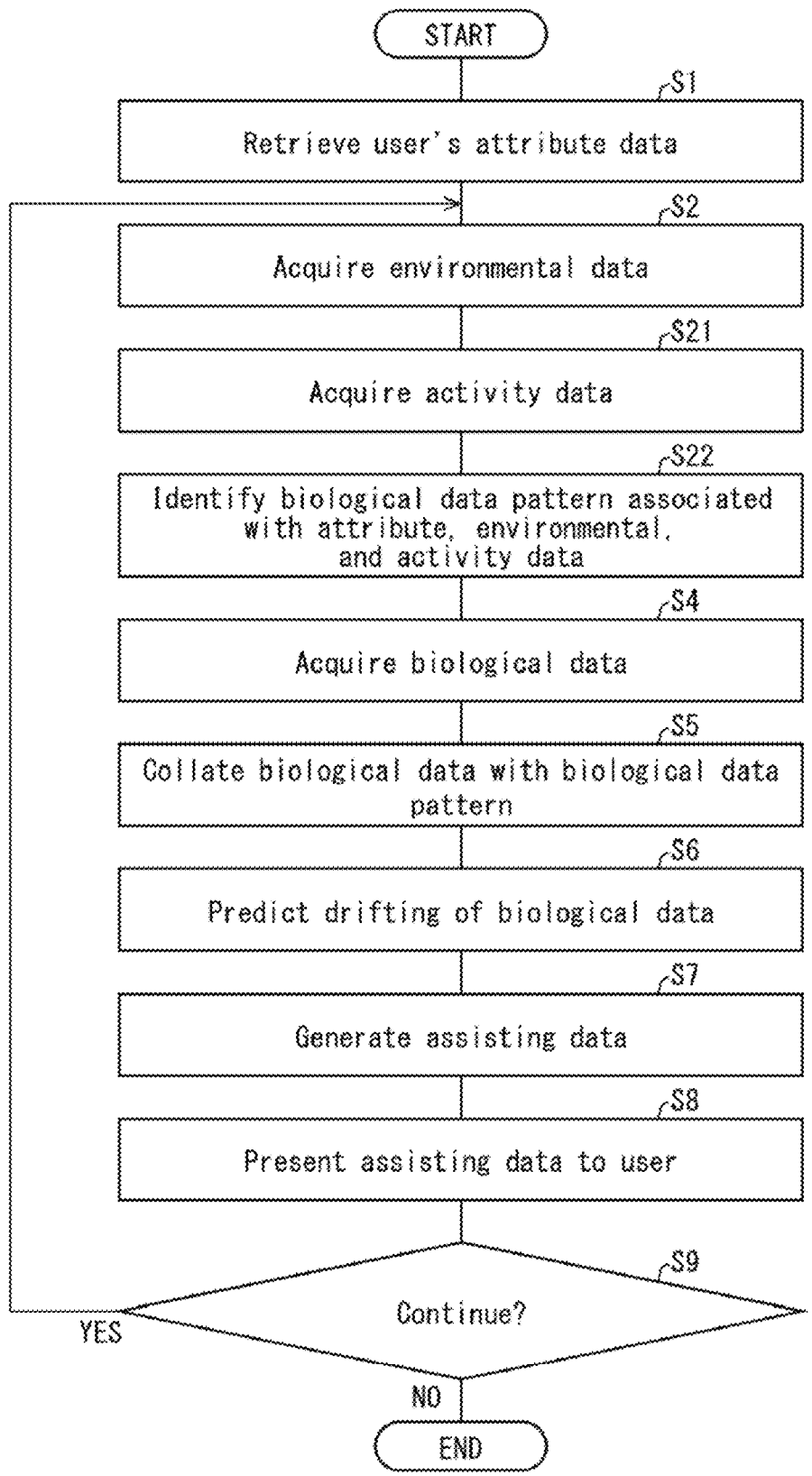
FIG. 9 is a flow chart depicting an example method of predicting biological data in accordance with Embodiment 3.

In S21 in FIG. 9, the activity level meter 50 acquires activity data. The activity level meter 50 may, for example, acquire activity data and transmit the acquired activity data to the biological data pattern identifying section 111 in response to a request from the biological data pattern identifying section 111. Alternatively, the activity level meter 50 may selectively transmit the latest set of activity data collected prior to such a request to the biological data pattern identifying section 111.

The biological data pattern identifying section 111 identifies, as a biological data pattern for use by the collating section 112, a biological data pattern associated with (1) the retrieved attribute data, (2) the environmental data acquired from the environmental sensor 20, and (3) the activity data acquired from the activity level meter 50 out of a plurality of biological data patterns stored in the memory unit 12 (S22). Collation is then done between this biological data pattern and the acquired biological data, which is followed by temporal prediction of biological data and generation of assisting data.

S2, S21, and S22 may be carried out simultaneously with S4 or after S4. In addition, S2 may be carried out simultaneously with S21 or after S21.

Major Effects

Since the body condition predicting device 10B uses a biological data pattern identified by taking the activity condition of the user into consideration in the collation of the biological data, the body condition predicting device 10B is capable of more accurately predicting drifting over time of the biological data.

Embodiment 4

Figure 10:
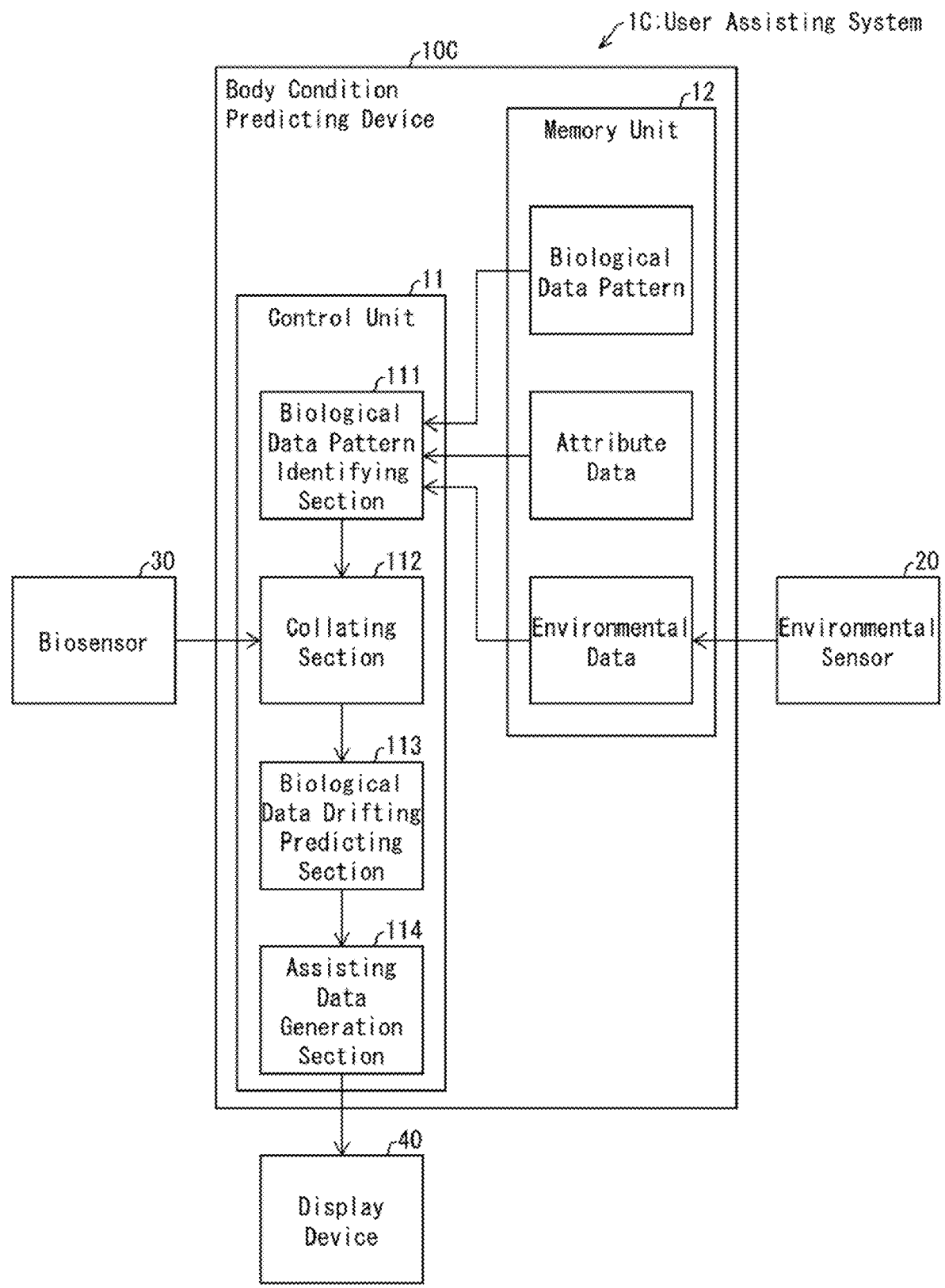
FIG. 10 is a diagram showing an example configuration of a user assisting system in accordance with Embodiment 4.

Another embodiment of the present invention will be described in reference to FIGS. 3 and 10. For convenience of description, members of the present embodiment that have the same function as members of any previous embodiment are indicated by the same reference numerals, and description thereof is omitted.

Configuration of Body Condition Predicting Device

First, a description will be given of an example body condition predicting device 10C in accordance with the present embodiment in reference to FIG. 10. FIG. 10 is a diagram showing an example configuration of a user assisting system 1C in accordance with the present embodiment. The user assisting system 1C differs from the user assisting system 1 of Embodiment 1 in that it includes the body condition predicting device 10C.

Specifically, in the body condition predicting device 10C of the present embodiment, the environmental sensor 20 acquires environmental data at a plurality of times, and the collating section 112 uses in collation a biological data pattern identified using this plurality of sets of environmental data acquired by the environmental sensor 20.

More specifically, the memory unit 12 in the body condition predicting device 10C temporarily stores the environmental data acquired by the environmental sensor 20 at a plurality of times. The biological data pattern identifying section 111 calculates, for example, an average of the values indicated by the sets of environmental data acquired by the environmental sensor 20 at a plurality of times (an average of the acquired temperatures when the environmental data is temperature). The biological data pattern identifying section 111 then identifies a biological data pattern for use in collation by the collating section 112, by using the average calculated as the environmental data.

Alternatively, the average of the values indicated by the sets of environmental data acquired in a prescribed period may be used as a value of environmental data after the prescribed period. In other words, the average may be shifted for each period after the prescribed period, without changing the length of the period.

Method of Predicting Body Condition

Next, a description will be given of a method of predicting biological data in reference to FIG. 3. S1, S4, and the subsequent steps in FIG. 3 are the same as those in Embodiment 1, and description of these steps is omitted.

In step S2 in FIG. 3, the environmental sensor 20 acquires environmental data at a plurality of times that is then stored in the memory unit 12. In step S3, the biological data pattern identifying section 111 calculates an average of the values indicated by a plurality of sets of environmental data stored in the memory unit 12. The biological data pattern identifying section 111 then uses the calculated average as a value indicated by the environmental data in identifying a biological data pattern for use in collation by the collating section 112 out of the biological data patterns stored in the memory unit 12. Collation is then done between this biological data pattern and the acquired biological data, which is followed by temporal prediction of biological data and generation of assisting data.

Major Effects

The values indicated by the environmental data acquired by the environmental sensor 20 may have a measurement error, for example, due to manufacturing variations of the environmental sensor 20. If the value indicated by a single set of environmental data has a measurement error and is used in identifying a biological data pattern, a biological data pattern may be identified that is ill-suited for the collation.

Since the body condition predicting device 10C identifies a biological data pattern by taking the environmental data acquired at a plurality of times into consideration, the body condition predicting device 10C is capable of, in the presence of a measurement error, identifying a biological data pattern while suppressing adverse effects of the measurement error. Therefore, if the acquired environmental data has irregularities, the body condition predicting device 10C can identify a biological data pattern for use in collation while suppressing the irregularities.

Embodiment 5

Figure 11:
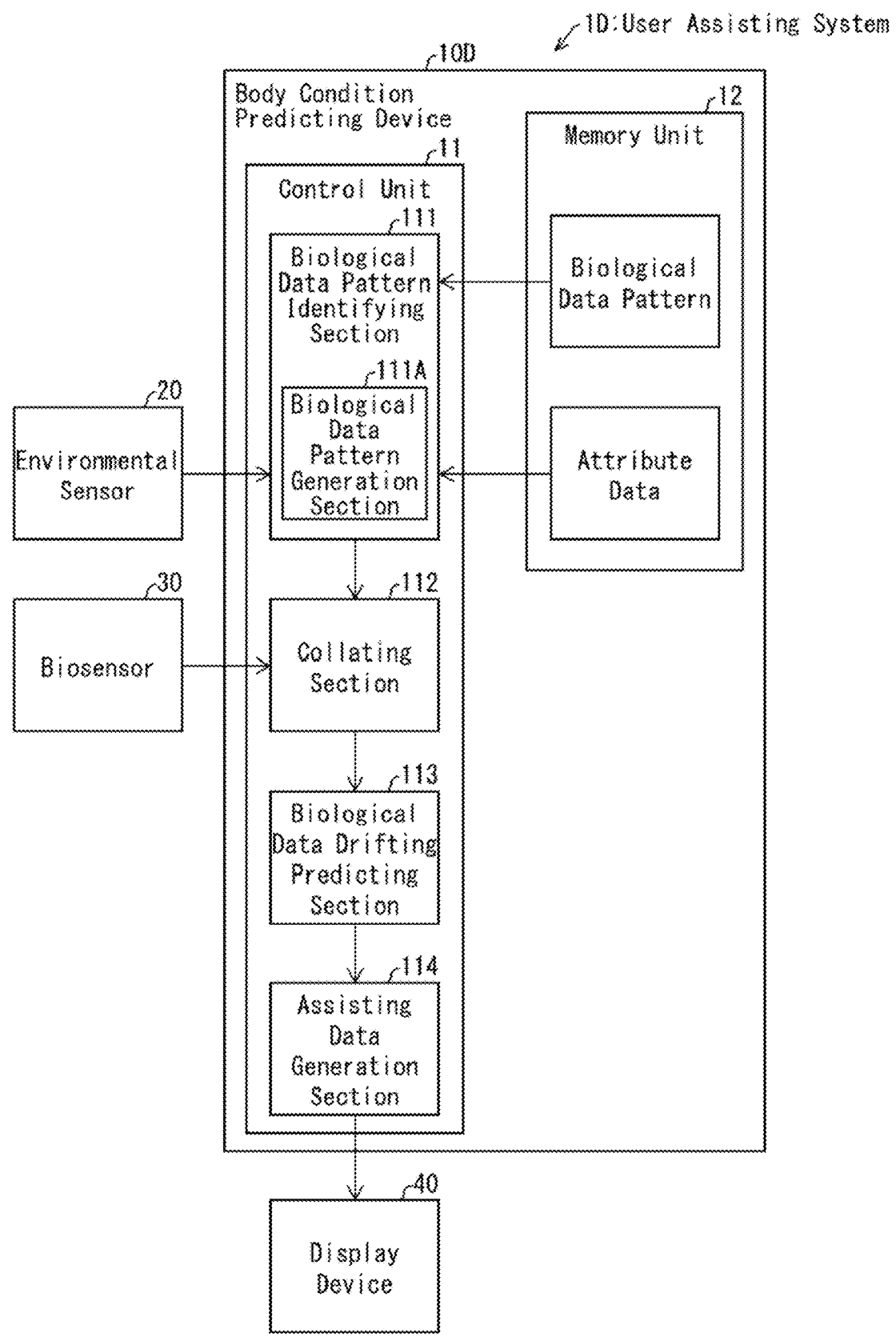
FIG. 11 is a diagram showing an example configuration of a user assisting system in accordance with Embodiment 5.

Another embodiment of the present invention will be described in reference to FIGS. 11 to 13. For convenience of description, members of the present embodiment that have the same function as members of any previous embodiment are indicated by the same reference numerals, and description thereof is omitted.

Configuration of Body Condition Predicting Device

First, a description will be given of an example body condition predicting device 10D in accordance with the present embodiment in reference to FIG. 11. FIG. 11 is a diagram showing an example configuration of a user assisting system 1D in accordance with the present embodiment. FIG. 12 is a diagram showing an example set of biological data patterns identified by the biological data pattern identifying section 111. The user assisting system 1D differs from the user assisting system 1 of Embodiment 1 in that it includes the body condition predicting device 10D.

The environmental sensor 20 acquires environmental data at a plurality of times for a plurality of sets of environmental data in the present embodiment as in Embodiment 4. The collating section 112 then uses in collation a biological data pattern identified using this plurality of sets of environmental data. The present embodiment differs from Embodiment 4 in how a biological data pattern is identified.

Specifically, the biological data pattern identifying section 111 in the control unit 11 includes a biological data pattern generation section 111A (pattern generation section). The biological data pattern generation section 111A generates a biological data pattern for use in collation by the collating section 112, by using a plurality of biological data patterns associated respectively with the plurality of sets of environmental data acquired by the environmental sensor 20.

More specifically, the biological data pattern generation section 111A, every time environmental data is acquired, identifies a biological data pattern associated with the environmental data out of the biological data patterns stored in the memory unit 12.

Assume, as an example, that the environmental temperature of the user is 20° C. up to time T1, starts to rise following time T1, reaches 25° C. at time T2, and remains at 25° C. after time T2. As an example, if the environmental sensor 20 acquires environmental data representing a temperature of 20° C. at time T1, the biological data pattern generation section 111A identifies a biological data pattern associated with this particular environmental data. Next, the environmental sensor 20 acquires, for example, environmental data representing a temperature of 25° C. at time T2, and the biological data pattern generation section 111A identifies a biological data pattern associated with this particular environmental data. It is also assumed that time 0 in the graph representing a biological data pattern matches the start of measurement of environmental data.

Then, as the biosensor 30 acquires biological data, the biological data pattern generation section 111A generates a biological data pattern for use in collation by the collating section 112, by using a biological data pattern identified before the biosensor 30 (or the body condition predicting device 10D) acquires that biological data. Specifically, if when environmental data is acquired, there is a biological data pattern identified before that environmental data is acquired, the biological data pattern generation section 111A uses the identified biological data pattern as a part of a biological data pattern used in collation (a part of the biological data pattern that precedes the acquisition of the environmental data). In addition, the biological data pattern generation section 111A uses the biological data pattern identified upon the acquisition of the environmental data as a part the biological data pattern used in collation (a part of the biological data pattern that follows the acquisition of the environmental data).

Figure 12:
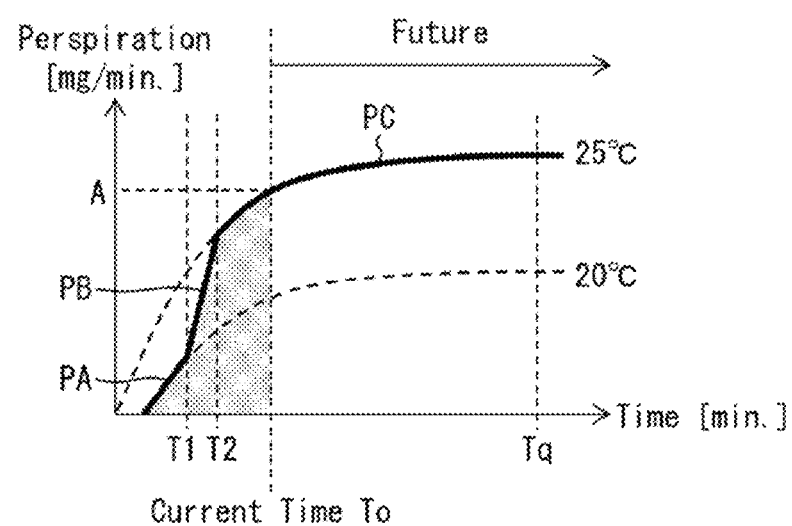
FIG. 12 is a diagram showing an example set of biological data patterns identified by a biological data pattern identifying section.
Figure 13:
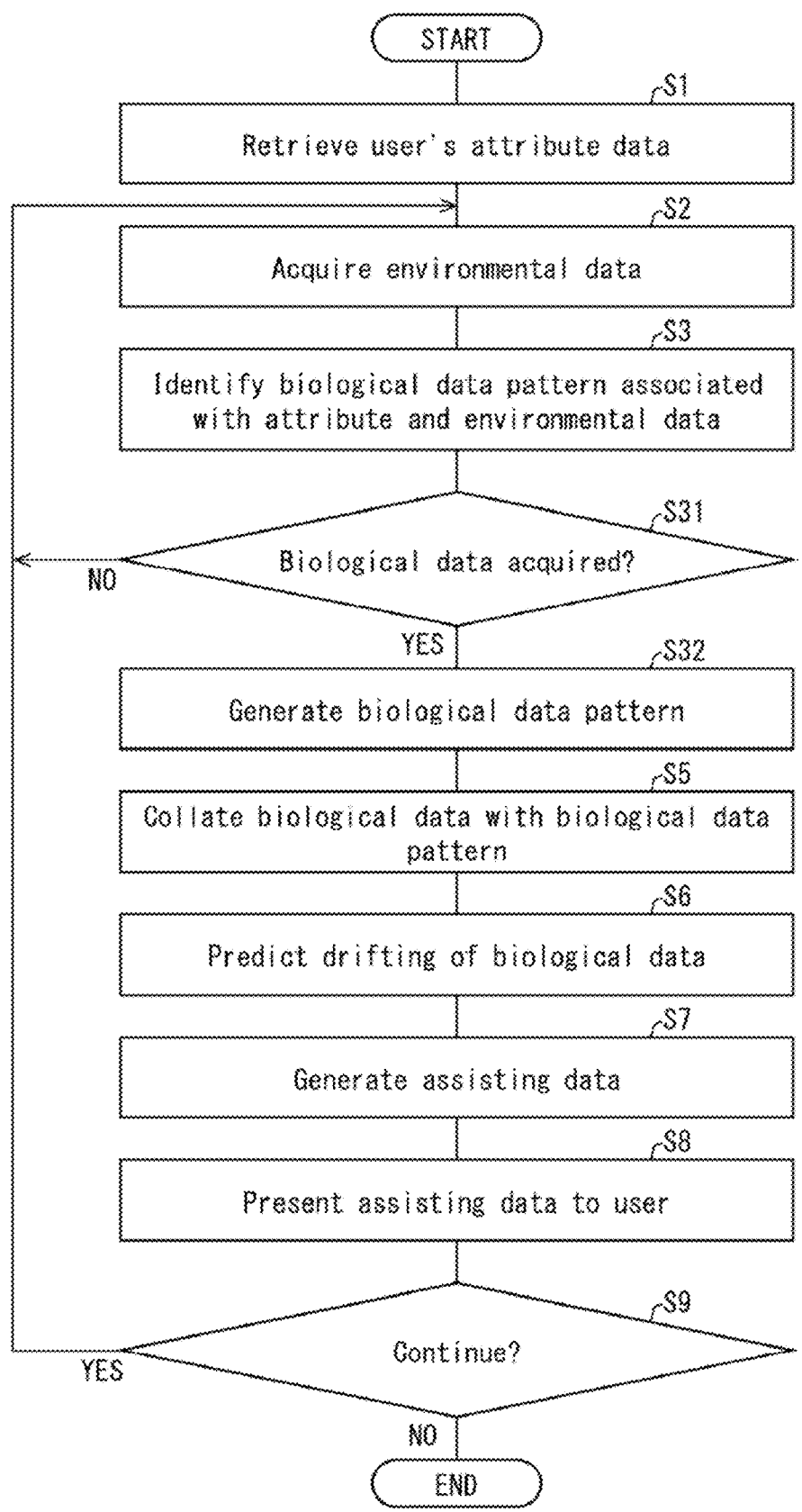
FIG. 13 is a flow chart depicting an example method of predicting biological data in accordance with Embodiment 5.

In the example in FIG. 12, the biological data pattern generation section 111A generates a biological data pattern including parts PA, PB, and PC. The part PA (up to time T1) is a biological data pattern applied if the acquired environmental data represents 20° C. The part PC (from time T2 and onwards) is a biological data pattern applied if the acquired environmental data represents 25° C. The part PB represents a collection of biological data patterns each applied upon acquisition of environmental data during the period from time T1 to T2.

If no environmental data is acquired and no biological data pattern is identified during the period from time T1 to T2, the biological data pattern generation section 111A may calculate biological data pattern values for that period in such a manner as to connect the biological data pattern value at time T1 to the biological data pattern value at time T2.

Method of Predicting Body Condition

Next, a description will be given of a method of predicting biological data in reference to FIG. 13. FIG. 13 is a flow chart depicting an example method of predicting biological data in accordance with the present embodiment. S1, S2, S5, and the subsequent steps in FIG. 13 are the same as those in Embodiment 1 or 4, and description of these steps is omitted.

For each set of environmental data, the biological data pattern generation section 111A identifies a biological data pattern associated with the set of environmental data and stores the identified biological data pattern in the memory unit 12 in step S3 in FIG. 3. In step S31, the biological data pattern generation section 111A determines whether or not the biosensor 30 has acquired biological data in response to a request from the collating section 112 (or whether or not the collating section 112 has acquired biological data from the biosensor 30).

If the biological data pattern generation section 111A determines that the biosensor 30 (or the collating section 112) has not acquired biological data (NO in step S31), the process returns to S2. To put it differently, every time the body condition predicting device 10D acquires environmental data, the body condition predicting device 10D identifies a biological data pattern associated with the environmental data and stores the identified biological data pattern in the memory unit 12. The body condition predicting device 10D repeats this process until the biosensor 30 (or the collating section 112) acquires biological data.

On the other hand, if the biological data pattern generation section 111A determines that the biosensor 30 (or the collating section 112) has acquired biological data (YES in step S31: the biological data acquisition step), the biological data pattern generation section 111A retrieves the biological data patterns that have so far been identified from the memory unit 12 and generates, using the retrieved biological data patterns, a biological data pattern for use in collation (S32). Then in step S5, the collating section 112 collates the biological data using the biological data pattern generated in step S32.

This is followed by temporal prediction of biological data and generation of assisting data. For example, the biological data drifting predicting section 113 operates in the same manner as in Embodiment 1 to determine time Tq (see FIG. 12) when there may occur an abnormal change in physical condition. In other words, the biological data drifting predicting section 113 is capable of predicting that if the user remains in the current environment (at 25° C. after temperature has changed in the example in FIG. 12), the user will experience an abnormal change in his/her physical condition in Tq-To minutes.

Major Effects

The biological data pattern generation section 111A generates a biological data pattern for use in collation by the collating section 112 on the basis of changes of the value indicated by the environmental data (temperature changes in the present embodiment) as described above. The body condition predicting device 10D is therefore capable of generating a biological data pattern by taking temporal environmental changes into consideration.

For example, if the environmental temperature changes, the biological data pattern also changes with the temperature. In the example in FIG. 12, the biological data pattern associated with a temperature of 20° C. differs from the biological data pattern associated with a temperature of 25° C.

If biological data is to be temporally predicted using perspiration levels straightaway as obtained from the biological data pattern (perspiration per prescribed unit time), the prediction is made using the biological data pattern identified every time environmental data is acquired (the latest biological data pattern). In contrast, if the prediction is made using a cumulative amount of perspiration instead of using the perspiration levels per prescribed unit time straightaway, different cumulative amounts are obtained from different biological data patterns. Therefore, if the biological data pattern is only updated in line with changes in the environment, it may be impossible to make an accurate prediction.

In the example in FIG. 12, the cumulative amount up to current time To is calculated as the size of the dotted area. If the biological data pattern used in collation is replaced with a biological data pattern associated with 25° C. upon acquiring environmental data representing 25° C., the resultant cumulative amount grows larger than the cumulative amount calculated using the biological data pattern generated by the biological data pattern generation section 111A. This difference in cumulative amount may lead to a deviation of the predicted timing. In the example in FIG. 12, the predicted timing comes earlier than when the biological data pattern generated by the biological data pattern generation section 111A is used, which in turn may end up in the user being forced to pay too much attention to his/her physical condition.

Meanwhile, if the cumulative amount is smaller than when the biological data pattern generated by the biological data pattern generation section 111A is used, the predicted timing is pushed into the future. The user may therefore fail to take suitable preventive measures before there occurs a change in his/her physical condition. The user may suffer heatstroke or face other serious health risks.

For these reasons, the biological data pattern generation section 111A generates a biological data pattern that is useful in a changing environment particularly when a cumulative amount is used in predicting a timing when there may occur a change in the user's physical condition.

The present embodiment has so far described assuming, as an example, that a plurality of sets of environmental data is acquired to generate a biological data pattern. Alternatively, the biological data pattern may be generated using the activity data described in Embodiment 3. In this alternative configuration, the biological data pattern generation section 111A generates a biological data pattern using a plurality of sets of activity data acquired by the activity level meter 50 (i.e., by taking temporal changes of activity data into consideration). The alternative configuration provides the same advantages as the previous configuration.

Embodiment 6

Figure 14:
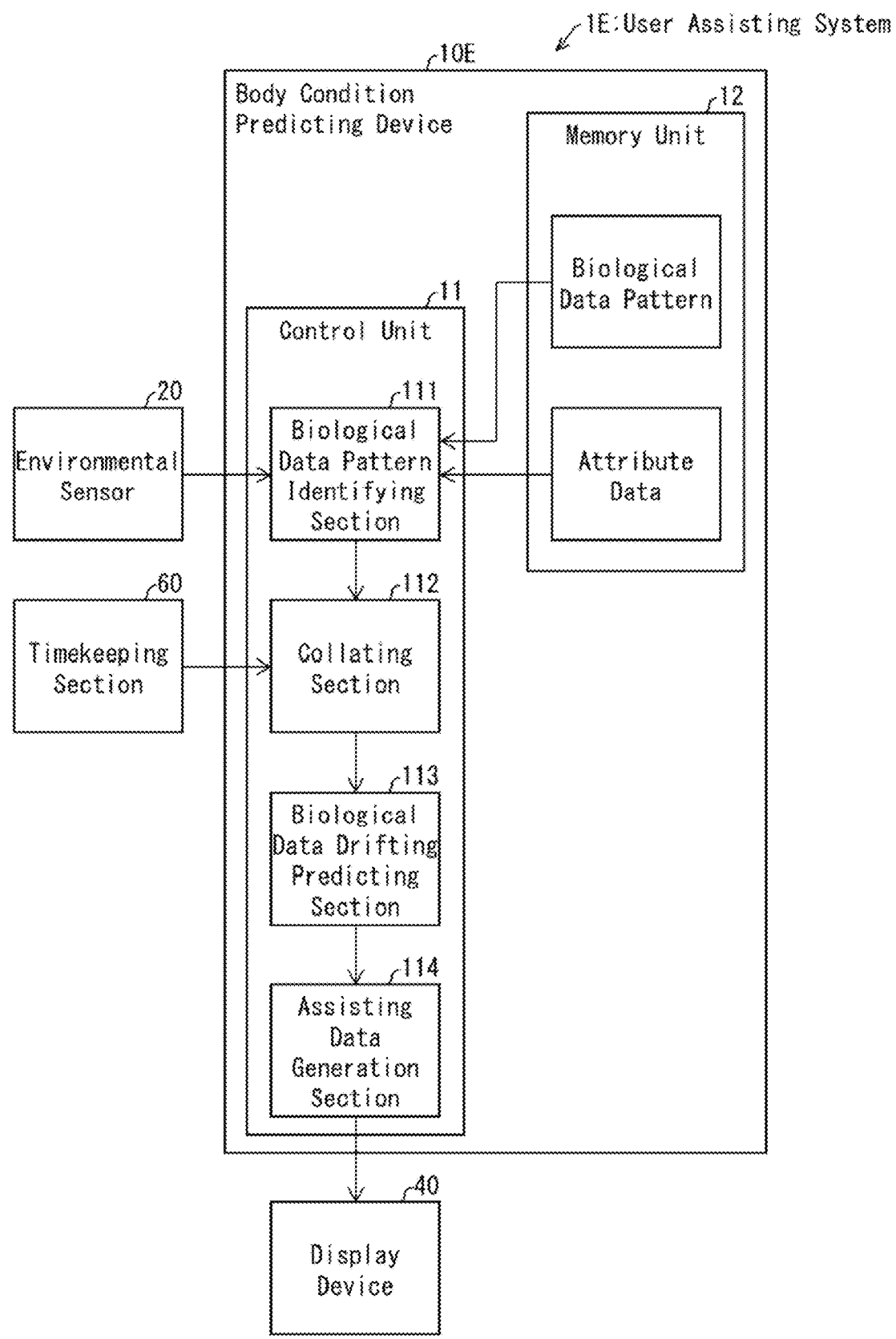
FIG. 14 is a diagram showing an example configuration of a user assisting system 1E in accordance with Embodiment 6.

Another embodiment of the present invention will be described in reference to FIGS. 14 and 15. For convenience of description, members of the present embodiment that have the same function as members of any previous embodiment are indicated by the same reference numerals, and description thereof is omitted.

Configuration of Body Condition Predicting Device

First, a description will be given of an example body condition predicting device 10E in accordance with the present embodiment in reference to FIG. 14. FIG. 14 is a diagram showing an example configuration of a user assisting system 1E in accordance with the present embodiment. The user assisting system 1E differs from the user assisting system 1 of Embodiment 1 in that it includes the body condition predicting device 10E and also in that it includes a timekeeping section 60 in place of the biosensor 30.

The timekeeping section 60 tracks time and is connected in a communicable manner to the body condition predicting device 10E. The timekeeping section 60 transmits a tracked current time as timekeeping data to the body condition predicting device 10E.

In the body condition predicting device 10E, the collating section 112 collates the current time tracked by the timekeeping section 60 instead of the biological data as in Embodiment 1 with a biological data pattern associated with either or both of the attribute data stored in the memory unit 12 and the environmental data acquired by the environmental sensor 20 (i.e., a biological data pattern identified by the biological data pattern identifying section 111). The biological data drifting predicting section 113 then predicts, on the basis of results of the collation by the collating section 112, drifting over time of the biological data of the user that will occur after the current time tracked by the timekeeping section 60.

In Embodiment 1, as described in reference to (b) of FIG. 2, the collating section 112 determines to what time a value A indicated by the biological data acquired by the biosensor 30 corresponds on the biological data pattern identified by the biological data pattern identifying section 111. The collating section 112, in the present embodiment, designates as current time To the current time tracked by the timekeeping section 60 and acquired as timekeeping data. In other words, the collating section 112 determines a time elapsed from the start of measurement of environmental data on the biological data pattern identified by the biological data pattern identifying section 111, based on the current time tracked by the timekeeping section 60. Therefore, the biological data drifting predicting section 113 predicts drifting over time of the biological data of the user that will occur on or after current time To, without the biosensor 30 having to acquire biological data. In other words, the body condition predicting device 10E is capable of making the prediction without having to acquire biological data.

The body condition predicting device 10E operates in the same manner as the body condition predicting device 10 of Embodiment 1, except that it acquires timekeeping data instead of biological data and designates the current time indicated in the timekeeping data as current time To.

It is assumed in the present embodiment that time 0 in the graph representing a biological data pattern in FIG. 2 matches, for example, a time when the timekeeping section 60 starts tracking time (the starting time of the measurement of environmental data).

Method of Predicting Body Condition

Next, a description will be given of a method of predicting biological data in reference to FIG. 15. FIG. 15 is a flow chart depicting an example method of predicting biological data in accordance with the present embodiment. S1 to S3, S6, and the subsequent steps in FIG. 15 are the same as those in Embodiment 1, and description of these steps is omitted.

Following the completion of S3, the timekeeping section 60 acquires a current time. The collating section 112 then acquires timekeeping data that represents the acquired current time from the timekeeping section 60. The timekeeping section 60 acquires timekeeping data and transmits the acquired timekeeping data to the collating section 112, for example, in response to a request from the collating section 112. The collating section 112 then collates the acquired timekeeping data with a biological data pattern identified in S3 and transmits results of the collation (e.g., data that represents the graph in (b) of FIG. 2) to the biological data drifting predicting section 113 (S42: the collating step).

The biological data drifting predicting section 113, in step S6, predicts drifting over time of biological data that will occur after the acquisition of the timekeeping data (i.e., after the current time) on the basis of the results of collation and transmits the prediction to the assisting data generation section 114.

S2 and S3 may be carried out simultaneously with S41 or after S41.

Major Effects

Since the body condition predicting device 10E collates the current time tracked by the timekeeping section with the biological data pattern identified by the biological data pattern identifying section 111, the body condition predicting device 10E is capable of predicting drifting over time of the biological data of the user that will occur after the current time. The body condition predicting device 10E can thus predict how soon from the current time a value indicated by biological data will reach approximately what level. It is hence possible to predict a timing when there may occur a change in the user's physical condition.

Since the body condition predicting device 10E collates biological data using the biological data pattern associated with attribute and/or environmental data similarly to Embodiment 1, it is possible to make the prediction in accordance with differences between individual users and/or different environmental conditions surrounding the users. The body condition predicting device 10E then generates assisting data on the basis of the prediction and presents the assisting data to the user. That enables the user to take preventive measures at a suitable time to avoid a change occurring in his/her physical condition.

Variation Examples

The body condition predicting device 10A to 10D of Embodiments 2 to 5 may acquire timekeeping data instead of biological data, which will be variation examples of the body condition predicting device 10E of Embodiment 6.

Specifically, (1) in the body condition predicting device 10E, the timekeeping section 60 may acquire timekeeping data at a plurality of times, and the collating section 112 may collate biological data using the acquired plurality of sets of timekeeping data, similarly to Embodiment 2. In this configuration, for example, the timekeeping section 60 may calculate an average value of the times represented by the plurality of sets of timekeeping data, and designate the average value as a current time for use in collation.

(2) In the body condition predicting device 10E, the collating section 112 may select one of the identified biological data patterns using a plurality of sets of timekeeping data (e.g., the average value described above), and the biological data drifting predicting section 113 may predict drifting over time of biological data using the biological data pattern selected by the collating section 112, similarly to a variation example of Embodiment 2.

(3) The user assisting system 1E may include an activity level meter 50 similarly to Embodiment 3. In addition, in the body condition predicting device 10E, the biological data pattern used in collation by the collating section 112 may be associated not only with attribute data and/or environmental data, but also with the activity data acquired by the activity level meter 50.

(4) In the body condition predicting device 10E, the environmental sensor 20 may acquire environmental data at a plurality of times, and the collating section 112 may collate biological data using a biological data pattern identified using the acquired plurality of sets of environmental data, similarly to Embodiment 4.

(5) In the body condition predicting device 10E, the biological data pattern generation section 111A may generate a biological data pattern for use in collation by the collating section 112, by using a plurality of biological data patterns associated respectively with a plurality of sets of environmental data, similarly to Embodiment 5.

The user assisting system 1E has been described as including a timekeeping section 60 in place of the biosensor 30. Alternatively, the user assisting system 1E may include both a biosensor 30 and a timekeeping section 60.

In this configuration, the body condition predicting device 10E, for example, collates biological data with a biological data pattern and also collates timekeeping data with a biological data pattern. The body condition predicting device 10E then predicts, on the basis of results of the collation, drifting over time of the biological data (e.g., a timing when there may occur an abnormal change in the user's physical condition) that will occur after the acquisition of the biological data and also after a current time (i.e., after the acquisition of the timekeeping data). If the timing predicted using the biological data differs from the timing predicted using the timekeeping data, the biological data drifting predicting section 113 may (1) designate an earlier one of the two predicted timings as the result of the prediction or (2) designate another timing obtained by a prescribed computation, such as an average value of the two timings, as the result of the prediction.

Software Implementation

The control blocks in the body condition predicting devices 10 and 10A to 10E (especially, the various sections in the control unit 11) may be implemented by logic circuits (hardware) fabricated, for example, in the form of an integrated circuit (IC chip) and may be implemented by software executed by a CPU (central processing unit).

In the latter form of implementation, the body condition predicting devices 10 and 10A to 10E include among others a CPU that executes instructions from programs or software by which various functions are implemented, a ROM (read-only memory) or like storage device (referred to as a "storage medium") containing the programs and various data in a computer-readable (or CPU-readable) format, and a RAM (random access memory) into which the programs are loaded. The computer (or CPU) then retrieves and executes the programs contained in the storage medium, thereby achieving the object of an aspect of the present invention. The storage medium may be a "non-transient, tangible medium" such as a tape, a disc, a card, a semiconductor memory, or programmable logic circuitry. The programs may be fed to the computer via any transmission medium (e.g., over a communications network or by broadcasting waves) that can transmit the programs. The present invention, in an aspect thereof, encompasses data signals on a carrier wave that are generated during electronic transmission of the programs.

Summation

The present invention, in aspect 1 thereof, is directed to a body condition predicting device (10, 10A to 10D) to be connected in a communicable manner to: a biological data acquisition section (biosensor 30) configured to acquire biological data representing a condition of a living body (user); and an environmental data acquisition section (environmental sensor 20) configured to acquire environmental data representing a condition of an environment surrounding the living body, the body condition predicting device including: a collating section (112) configured to collate the biological data acquired by the biological data acquisition section with a biological data pattern (P1, P2, P3) representing drifting over time of the biological data, the biological data pattern being associated with either or both attribute data representing an attribute of the living body and the environmental data acquired by the environmental data acquisition section; and a predicting section (biological data drifting predicting section 113) configured to predict, based on a result of collation performed by the collating section, the drifting over time of the biological data that occurs after the biological data acquisition section acquires the biological data.

In this configuration, the biological data acquisition section is capable of predicting drifting over time that will occur after the acquisition of the biological data, by collating the acquired biological data with a biological data pattern. The body condition predicting device can therefore predict how soon from the acquisition of biological data a value indicated by the biological data will reach approximately what level.

It is hence possible to predict a timing when there may occur a change in the physical condition of the user (living body) after the acquisition of the biological data. That enables the user to take preventive measures at a suitable time to avoid such a change occurring in his/her physical condition.

In aspect 2 of the present invention, the body condition predicting device of aspect 1 preferably further includes an assisting data generation section (114) configured to generate, based on the drifting over time of the biological data predicted by the predicting section, assisting data that indicates a measure that reduces possibility of a change occurring in physical condition of the living body.

In this configuration, the user can check the assisting data and take suitable preventive measures to avoid a change occurring in his/her physical condition.

In aspect 3 of the present invention, the body condition predicting device of aspect 1 or 2 is preferably such that the predicting section predicts a timing when either a value indicated on the biological data pattern by the biological data or a cumulative amount of this value reaches a prescribed level.

This configuration is capable of predicting a timing when either a value indicated by the biological data or a cumulative amount of this value will reach a prescribed level (e.g., a value at which there may occur a change in the physical condition). Therefore, the user can take preventive measures before a predicted timing (i.e., at a suitable time) to avoid such a change occurring in his/her physical condition.

In aspect 4 of the present invention, the body condition predicting device of any one of aspects 1 to 3 preferably further includes an identifying section (biological data pattern identifying section 111) configured to identify either one or both of (1) one of biological data patterns associated with predetermined attribute values representing the attribute, the one of biological data patterns corresponding to the attribute data, and (2) one of biological data patterns associated with predetermined environmental values representing the prescribed condition of the environment, the one of biological data patterns corresponding to the environmental data, wherein the collating section collates the biological data using the biological data pattern or patterns identified by the identifying section.

This configuration is capable of identifying a biological data pattern for use in collation from a plurality of biological data patterns prepared in advance, simply by acquiring attribute data and environmental data.

In aspect 5 of the present invention, the body condition predicting device of any one of aspects 1 to 4 is preferably such that: the biological data acquisition section acquires the biological data at a plurality of times; and the collating section collates the biological data using a plurality of sets of biological data acquired by the biological data acquisition section.

This configuration is capable of accurately determining, on the biological data pattern used in collation, the time when the biological data is acquired even when the acquired biological data has irregularities. The configuration is hence capable of accurately predicting drifting over time of the biological data.

In aspect 6 of the present invention, the body condition predicting device of aspect 5 is preferably such that: a plurality of biological data patterns is identified for use in collation by the collating section; the collating section selects one of the identified biological data patterns using the sets of biological data; and the predicting section predicts the drifting over time of the biological data using the biological data pattern selected by the collating section.

This configuration is capable of selecting a biological data pattern that is more suited to the user's condition. It is hence possible to more accurately predict the drifting over time of the biological data.

In aspect 7 of the present invention, the body condition predicting device of any one of aspects 1 to 6 is preferably such that: the environmental data acquisition section acquires the environmental data at a plurality of times; and the collating section collates the biological data using a biological data pattern or patterns identified using a plurality of sets of environmental data acquired by the environmental data acquisition section.

This configuration, if the acquired environmental data has irregularities, can use the biological data pattern in collation while suppressing the irregularities.

In aspect 8 of the present invention, the body condition predicting device of aspect 7 preferably further includes a pattern generation section (biological data pattern generation section 111A) configured to generate, using a plurality of biological data patterns associated respectively with the sets of environmental data acquired by the environmental data acquisition section, a biological data pattern for use in collation by the collating section.

This configuration is capable of generating a biological data pattern by taking temporal environmental changes into consideration. The configuration is capable of accurately predicting particularly a timing when a cumulative amount of a value indicated on a biological data pattern by the biological data will reach a prescribed level.

In aspect 9 of the present invention, the body condition predicting device of any one of aspects 1 to 8 is preferably further connected in a communicable manner to an activity data acquisition section (activity level meter 50) configured to acquire activity data representing an activity condition of the living body, wherein the biological data pattern or patterns for use in collation by the collating section is further associated with the activity data acquired by the activity data acquisition section.

Since this configuration uses a biological data pattern identified by taking the activity condition of the user into consideration in the collation of the biological data, the configuration is capable of more accurately predicting drifting over time of the biological data.

In aspect 10 of the present invention, the body condition predicting device of any one of aspects 1 to 9 is preferably such that the environmental data acquisition section acquires data representing either one or both of temperature and humidity of the environment as the environmental data.

This configuration is capable of predicting the drifting over time of the biological data using a biological data pattern associated with either one or both of the temperature and humidity of the environment.

In aspect 11 of the present invention, the body condition predicting device of any one of aspects 1 to 10 is preferably such that the biological data acquisition section acquires data representing at least any one of a skin surface water content, body temperature, and heart rate of the living body as the biological data.

This configuration enables the use of at least any one of the skin surface water content, body temperature, and heart rate as the biological data.

In aspect 12 of the present invention, the body condition predicting device of any one of aspects 1 to 11 is preferably such that the attribute includes at least any one of a physique, age, and gender of the living body.

This configuration is capable of predicting the drifting over time of the biological data using a biological data pattern associated with at least any one of the physique, age, and gender of the user.

The present invention, in aspect 13 thereof, is directed to a method of predicting a body condition, the method including: the biological data acquisition step (S4) of acquiring biological data representing a condition of a living body; the environmental data acquisition step (S2) of acquiring environmental data representing a condition of an environment surrounding the living body; the collating step (S5) of collating the biological data acquired in the biological data acquisition step with a biological data pattern representing drifting over time of the biological data, the biological data pattern being associated with either or both attribute data representing an attribute of the living body and the environmental data acquired in the environmental data acquisition step; and the predicting step (S6) of predicting, based on a result of collation performed in the collating step, the drifting over time of the biological data that occurs after the biological data is acquired in the biological data acquisition step.

The method is, similarly to aspect 1, capable of predicting a timing when there may occur a change in the physical condition of the user (living body) after the acquisition of the biological data. That enables the user to take preventive measures at a suitable time to avoid such a change occurring in his/her physical condition.

The present invention, in aspect 14 thereof, is directed to a body condition predicting program causing a computer to function as the body condition predicting device of aspect 1, the body condition predicting program implementing at least the collating section and the predicting section on the computer.

The present invention, in aspect 15 thereof, is directed to a body condition predicting device (10E) to be connected in a communicable manner to: a timekeeping section (60); and an environmental data acquisition section (environmental sensor 20) configured to acquire environmental data representing a condition of an environment surrounding a living body, the body condition predicting device including: a collating section (112) configured to collate a current time tracked by the timekeeping section with a biological data pattern representing (P1, P2, P3) drifting over time of biological data, the biological data pattern being associated with either or both attribute data representing an attribute of the living body and the environmental data acquired by the environmental data acquisition section; and a predicting section (biological data drifting predicting section 113) configured to predict, based on a result of collation performed by the collating section, the drifting over time of the biological data that occurs after the current time tracked by the timekeeping section.

This configuration is capable of predicting drifting over time that will occur after the current time, by collating the current time tracked by the timekeeping section with the biological data pattern. The configuration can thus predict how soon from the acquisition of the current time a value indicated by biological data will reach approximately what level.

It is hence possible to predict a timing when there may occur a change in the physical condition of the user (living body) after the current time. That enables the user to take preventive measures at a suitable time to avoid such a change occurring in his/her physical condition.

The body condition predicting device in each aspect of the present invention may be computer-implemented. When this is the case, the aspect of the present invention encompasses a body condition predicting program that, when executed on a computer, causes the computer to function as those units in the body condition predicting device (software elements) to implement the body condition predicting device and also encompasses a computer-readable storage medium containing the program.

Aspects of Present Invention Expressed in Different Words

Aspects of the present invention may be described as follows.

(1) The present invention, in an aspect thereof, is directed to a user assisting device (body condition predicting device) including: a biological information acquisition unit configured to acquire biological information of a user; an attribute information storage unit configured to store attribute information of the user; an environmental information acquisition unit configured to acquire environmental information; a biological information predicting unit configured to predict biological information for a future time as seen from a current time using the biological information acquired from the biological information acquisition unit and a temporal biological information pattern associated with either or both of the environmental information acquired from the environmental information acquisition unit and the attribute information of the user retrieved from the attribute information storage unit; and an assisting information generation unit configured to generate, using the biological information predicted by the biological information predicting unit, assisting information including information for a future time as seen from the current time.

(2) The user assisting device in accordance with an aspect of the present invention is preferably such that the biological information predicting unit predicts biological information for a future time as seen from the current time using biological information acquired from the biological information acquisition unit for a plurality of times.

(3) The user assisting device in accordance with an aspect of the present invention preferably further includes an activity information acquisition unit configured to acquire activity information of the user, wherein the biological information predicting unit predicts biological information for a future time as seen from the current time using the biological information acquired from the biological information acquisition unit and a temporal biological information pattern associated with the activity information acquired from the activity information acquisition unit and also with either or both of the environmental information acquired from the environmental information acquisition unit and the attribute information of the user retrieved from the attribute information storage unit.

(4) The user assisting device in accordance with an aspect of the present invention is preferably such that the attribute information includes any of an age and gender of the user and information on a physique of the user.

(5) The user assisting device in accordance with an aspect of the present invention is preferably such that the environmental information acquisition unit is a sensor that measures ambient temperature and/or humidity.

(6) The user assisting device in accordance with an aspect of the present invention is preferably such that the biological information acquisition unit is a sensor that measures a skin surface water content of the user.

(7) The user assisting device in accordance with an aspect of the present invention is preferably such that the biological information acquisition unit is a sensor that measures a body temperature of the user.

(8) The user assisting device in accordance with an aspect of the present invention is preferably such that the biological information acquisition unit is a sensor that measures a heart rate of the user.

(9) The present invention, in another aspect thereof, is directed to a method of assisting a user (method of predicting a body condition) including: the biological information acquisition step of acquiring biological information of the user; the attribute information acquisition step of retrieving attribute information from an attribute information storage unit storing attribute information of the user; the environmental information acquisition step of acquiring environmental information; the biological information predicting step of predicting biological information for a future time as seen from a current time using the biological information acquired in the biological information acquisition step and a temporal biological information pattern associated with either or both of the environmental information and the attribute information; and the assisting information generation step of generating assisting information including information for a future time as seen from the current time using the biological information predicted in the biological information predicting step.

Additional Remarks

The aspects of the present invention are not limited to the description of the embodiments above and may be altered within the scope of the claims. Embodiments based on a proper combination of technical means disclosed in different embodiments are encompassed in the technical scope of the aspects of the present invention. Furthermore, a new technological feature may be created by combining different technological means disclosed in the embodiments.

CROSS-REFERENCE TO RELATED APPLICATIONS

The present application claims the benefit of priority to Japanese Patent Application, Tokugan, No. 2016-098202, filed on May 16, 2016, the entire contents of which are incorporated herein by reference.

REFERENCE SIGNS LIST 10, 10A, 10B, 10C, 10D, 10E Body Condition Predicting Device
20 Environmental Sensor (Environmental Data Acquisition Section)
30 Biosensor (Biological Data Acquisition Section)
50 Activity Level Meter (Activity Data Acquisition Section)
60 Timekeeping Section
111 Biological Data Pattern Identifying Section (Identifying Section)
111A Biological Data Pattern Generation Section (Pattern Generation Section)
112 Collating Section
113 Biological Data Drifting Predicting Section (Predicting Section)
114 Assisting Data Generation Section
P1, P2, P3 Biological Data Pattern

The invention claimed is:

1. A body condition predicting device to be connected in a communicable manner to: a biological data acquisition section configured to acquire biological data representing a condition of a living body; an environmental data acquisition section configured to acquire environmental data representing a condition of an environment surrounding the living body; and a presentation section, said body condition predicting device comprising:

a collating section configured to collate the biological data acquired by the biological data acquisition section with a biological data pattern representing drifting over time of the biological data, the biological data pattern being associated with either or both attribute data representing an attribute of the living body and the environmental data acquired by the environmental data acquisition section;

a predicting section configured to predict, based on a result of collation performed by the collating section, the drifting over time of the biological data that occurs after the biological data acquisition section acquires the biological data;

an assisting data generation section configured to generate, based on the drifting over time of the biological data predicted by the predicting section, assisting data that indicates a measure that reduces possibility of a change occurring in physical condition of the living body; and an identifying section configured to identify either one or both of (1) one of biological data patterns associated with predetermined attribute values representing the attribute, the one of biological data patterns corresponding to the attribute data, and (2) one of biological data patterns associated with predetermined environmental values representing the prescribed condition of the environment, the one of biological data patterns corresponding to the environmental data, wherein in each of the biological data patterns shown in the (1) and (2), a correspondence between biological data representing a condition of a living body and a time having elapsed from a referential time point is set in advance, wherein the collating section determines a time that corresponds to a value of the biological data acquired by the biological data acquisition section on the biological data pattern identified by the identifying section, and the predicting section predicts drifting over time of the biological data that will occur after the determined time on the identified biological data pattern, and wherein the body condition predicting device causes the presentation section to present the assisting data generated by the assisting data generation section.

2. The body condition predicting device according to claim 1, wherein the predicting section predicts a timing when either a value indicated on the biological data pattern by the biological data or a cumulative amount of this value reaches a prescribed level.

3. The body condition predicting device according to claim 1, wherein:
the biological data acquisition section acquires the biological data at a plurality of times; and
the collating section collates the biological data using a plurality of sets of biological data acquired by the biological data acquisition section.

4. The body condition predicting device according to claim 1, wherein:
the biological data acquisition section acquires the biological data at a plurality of times;
the identifying section identifies a plurality of biological data patterns for use in collation by the collating section;
the collating section selects one of the identified biological data patterns using the sets of biological data; and
the predicting section predicts the drifting over time of the biological data using the biological data pattern selected by the collating section.

5. The body condition predicting device according to claim 1, wherein:
the environmental data acquisition section acquires the environmental data at a plurality of times; and
the collating section collates the biological data using a biological data pattern or patterns identified by the identifying section by using a plurality of sets of environmental data acquired by the environmental data acquisition section.

6. The body condition predicting device according to claim 5, further comprising a pattern generation section configured to generate, using a plurality of biological data patterns associated respectively with the sets of environmental data acquired by the environmental data acquisition section, a biological data pattern for use in collation by the collating section.

7. The body condition predicting device according to claim 1, to be further connected in a communicable manner to an activity data acquisition section configured to acquire activity data representing an activity condition of the living body, wherein the biological data pattern or patterns for use in collation by the collating section is further associated with the activity data acquired by the activity data acquisition section.

8. The body condition predicting device according to claim 1, wherein the environmental data acquisition section acquires data representing either one or both of temperature and humidity of the environment as the environmental data.

9. The body condition predicting device according to claim 1, wherein the biological data acquisition section acquires data representing at least any one of a skin surface water content, body temperature, and heart rate of the living body as the biological data.

10. The body condition predicting device according to claim 1, wherein the attribute includes at least any one of a physique, age, and gender of the living body.

11. The body condition predicting device according to claim 1, wherein:
the biological data acquisition section acquires the biological data at a plurality of times;
the identifying section identifies (i) one biological data pattern corresponding to either one or both of the attribute data and the environmental data and (ii) at least one biological data pattern having properties similar to those of the one biological data pattern; and
the collating section (i) selects, from a plurality of sets of biological data patterns identified by the identifying section, a biological data pattern, which has the highest match level for an approximation curve calculated from a plurality of sets of biological data acquired by the biological data acquisition section, and (ii) uses the selected biological data pattern in collation.

12. A method of predicting a body condition, the method being carried out by a body condition predicting device configured to predict a condition of a living body, the body condition predicting device being connected in a communicable manner to a presentation section, said method comprising:
the biological data acquisition step of acquiring biological data representing the condition of the living body;
the environmental data acquisition step of acquiring environmental data representing a condition of an environment surrounding the living body;
the collating step of collating the biological data acquired in the biological data acquisition step with a biological data pattern representing drifting over time of the biological data, the biological data pattern being associated with either or both attribute data representing an attribute of the living body and the environmental data acquired in the environmental data acquisition step;
the predicting step of predicting, based on a result of collation performed in the collating step, the drifting over time of the biological data that occurs after the biological data is acquired in the biological data acquisition step;
the generation step of generating, based on the drifting over time of the biological data predicted in the predicting step, assisting data that indicates a measure that reduces possibility of a change occurring in physical condition of the living body; and
the identification step of identifying either one or both of (1) one of biological data patterns associated with predetermined attribute values representing the attribute, the one of biological data patterns corresponding to the attribute data, and (2) one of biological data patterns associated with predetermined environmental values representing the prescribed condition of the environment, the one of biological data patterns corresponding to the environmental data,
wherein in each of the biological data patterns shown in the (1) and (2), a correspondence between biological data representing a condition of a living body and a time having elapsed from a referential time point is set in advance, and wherein the collating step includes determining a time that corresponds to a value of the biological data acquired in the biological data acquisition step on the biological data pattern identified in the identification step, and the predicting step includes predicting drifting over time of the biological data that will occur after the determined time on the identified biological data pattern, said method further comprising:

the presentation step of causing the presentation section to present the assisting data generated in the generation step.

13. A body condition predicting program causing a computer to function as the body condition predicting device according to claim 1, said body condition predicting program implementing the collating section and the predicting section on the computer.

* * * * *